United States Patent
Akkurt

(10) Patent No.: US 7,755,354 B2
(45) Date of Patent: Jul. 13, 2010

(54) SYSTEM AND METHODS FOR T1-BASED LOGGING

(75) Inventor: Ridvan Akkurt, Kingwood, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 12/264,637

(22) Filed: Nov. 4, 2008

(65) Prior Publication Data

US 2009/0093962 A1    Apr. 9, 2009

Related U.S. Application Data

(62) Division of application No. 11/731,121, filed on Mar. 29, 2007, now Pat. No. 7,501,818, which is a division of application No. 10/957,406, filed on Oct. 1, 2004, now Pat. No. 7,199,580.

(60) Provisional application No. 60/508,442, filed on Oct. 3, 2003.

(51) Int. Cl.
   *G01V 3/00*    (2006.01)
(52) U.S. Cl. .......................... 324/303; 324/300
(58) Field of Classification Search .......... 324/300–322
   See application file for complete search history.

(56) References Cited

U.S. PATENT DOCUMENTS

| | | |
|---|---|---|
| 1,158,959 A | 11/1915 | Beach |
| 2,262,655 A | 11/1941 | Seale |
| 2,705,790 A | 4/1955 | Hahn |
| 2,912,641 A | 11/1959 | Ruble |
| 2,973,471 A | 2/1961 | Armistead et al. |
| 3,011,554 A | 12/1961 | Desbrandes et al. |
| 3,205,477 A | 9/1965 | Kalbfell |
| 3,209,588 A | 10/1965 | Terry |
| 3,212,574 A | 10/1965 | Fox |
| 3,213,357 A | 10/1965 | Brown et al. |
| 3,360,716 A | 12/1967 | Bloom et al. |
| 3,395,337 A | 7/1968 | Varian |
| 3,402,344 A | 9/1968 | Brown et al. |
| 3,427,532 A | 2/1969 | Nelson |

(Continued)

FOREIGN PATENT DOCUMENTS

DE        1030940        5/1958

(Continued)

OTHER PUBLICATIONS

Abragam, The Principles of Nuclear Magnetism, 1961 (whole book).

(Continued)

*Primary Examiner*—Brij B Shrivastav
(74) *Attorney, Agent, or Firm*—Jones Day

(57) ABSTRACT

System and methods for using nuclear magnetic resonance (MR) $T_1$ measurements for wireline, LWD and MWD applications and down-hole NMR fluid analyzers. The $T_1$ measurements are characterized by insensitivity to motion, as the detrimental effects arising from tool motion or fluid flow are effectively reduced or eliminated. $T_1$ measurements alone or in combination with other standard oil field measurements are shown to provide efficient data acquisition resulting in compact and robust data sets, the potential for substantially increased logging speeds, and simple methods for fluid typing, including direct and robust identification of gas.

22 Claims, 16 Drawing Sheets

U.S. PATENT DOCUMENTS

| | | |
|---|---|---|
| 3,452,592 A | 7/1969 | Voetter |
| 3,453,433 A | 7/1969 | Alger et al. |
| 3,508,438 A | 4/1970 | Alger et al. |
| 3,528,000 A | 9/1970 | Schwede |
| 3,567,935 A | 3/1971 | Nagel |
| 3,567,936 A | 3/1971 | Tittman |
| 3,577,782 A | 5/1971 | Aitken |
| 3,590,228 A | 6/1971 | Burke |
| 3,593,116 A | 7/1971 | Culpepper |
| 3,617,867 A | 11/1971 | Herzog |
| 3,638,484 A | 2/1972 | Tixier |
| 3,657,730 A | 4/1972 | Robinson et al. |
| 3,667,035 A | 5/1972 | Slichter |
| 3,777,560 A | 12/1973 | Guignard |
| 3,784,898 A | 1/1974 | Darley et al. |
| 3,896,668 A | 7/1975 | Anderson et al. |
| 4,210,018 A | 7/1980 | Brieger |
| 4,291,271 A | 9/1981 | Lauffer |
| 4,292,842 A | 10/1981 | Hallmark |
| 4,310,887 A | 1/1982 | Suau |
| 4,339,948 A | 7/1982 | Hallmark |
| 4,350,955 A | 9/1982 | Jackson et al. |
| 4,424,487 A | 1/1984 | Lauffer |
| 4,470,456 A | 9/1984 | Moutray et al. |
| 4,479,564 A | 10/1984 | Tanguy |
| 4,528,508 A | 7/1985 | Vail, III |
| 4,536,711 A | 8/1985 | King et al. |
| 4,536,714 A | 8/1985 | Clark |
| 4,625,547 A | 12/1986 | Lyle, Jr. |
| 4,629,986 A | 12/1986 | Clow et al. |
| 4,629,987 A | 12/1986 | King et al. |
| 4,638,251 A | 1/1987 | King |
| 4,656,422 A | 4/1987 | Vail, III et al. |
| 4,686,364 A | 8/1987 | Herron |
| 4,700,142 A | 10/1987 | Kuckess |
| 4,707,658 A | 11/1987 | Frahm et al. |
| 4,710,713 A | 12/1987 | Strikman |
| 4,714,881 A | 12/1987 | Givens |
| 4,717,876 A | 1/1988 | Masi et al. |
| 4,717,877 A | 1/1988 | Taicher et al. |
| 4,717,878 A | 1/1988 | Taicher et al. |
| 4,728,892 A | 3/1988 | Vinegar et al. |
| 4,742,459 A | 5/1988 | Lasseter et al. |
| 4,761,889 A | 8/1988 | Cobern et al. |
| 4,769,602 A | 9/1988 | Vinegar et al. |
| 4,777,464 A | 10/1988 | Takabatashi et al. |
| 4,783,742 A | 11/1988 | Peter |
| 4,785,245 A | 11/1988 | Lew et al. |
| 4,792,757 A | 12/1988 | Vail, III et al. |
| RE32,913 E | 4/1989 | Clark |
| 4,825,163 A | 4/1989 | Yabusaki et al. |
| 4,829,252 A | 5/1989 | Kaufman |
| 4,860,581 A | 8/1989 | Zimmerman et al. |
| 4,875,013 A | 10/1989 | Murakami et al. |
| 4,885,540 A | 12/1989 | Snoddy et al. |
| 4,890,487 A | 1/1990 | Dussan V. et al. |
| 4,899,112 A | 2/1990 | Clark et al. |
| 4,931,760 A | 6/1990 | Yamaguchi et al. |
| 4,933,638 A | 6/1990 | Kenyon et al. |
| 4,933,640 A | 6/1990 | Kuckes |
| 4,936,139 A | 6/1990 | Zimmerman et al. |
| 4,939,648 A | 7/1990 | O'Neill et al. |
| 4,949,045 A | 8/1990 | Clark et al. |
| 4,951,749 A | 8/1990 | Carroll |
| 4,956,921 A | 9/1990 | Coles |
| 4,958,125 A | 9/1990 | Jardine et al. |
| 4,987,368 A | 1/1991 | Vinegar |
| 4,994,777 A | 2/1991 | Leupold et al. |
| 5,023,551 A | 6/1991 | Kleinberg et al. |
| 5,055,787 A | 10/1991 | Kleinberg et al. |
| 5,055,788 A | 10/1991 | Kleinberg et al. |
| 5,056,595 A | 10/1991 | Desbrandes |
| 5,122,746 A | 6/1992 | King et al. |
| 5,138,263 A | 8/1992 | Towle |
| 5,200,699 A | 4/1993 | Baldwin et al. |
| 5,212,447 A | 5/1993 | Paltiel |
| 5,233,866 A | 8/1993 | Desbrandes |
| 5,235,285 A | 8/1993 | Clark et al. |
| 5,265,015 A | 11/1993 | Auzerais et al. |
| 5,269,180 A | 12/1993 | Dave et al. |
| 5,279,153 A | 1/1994 | Dussan et al. |
| 5,280,243 A | 1/1994 | Miller et al. |
| 5,291,137 A | 3/1994 | Freedman |
| 5,293,931 A | 3/1994 | Nichols et al. |
| 5,299,128 A | 3/1994 | Antoine et al. |
| 5,309,098 A | 5/1994 | Coates et al. |
| 5,329,448 A | 7/1994 | Rosthal |
| 5,329,811 A | 7/1994 | Schultz et al. |
| 5,337,822 A | 8/1994 | Massie et al. |
| 5,349,184 A | 9/1994 | Wraight |
| 5,350,925 A | 9/1994 | Watson |
| 5,359,324 A | 10/1994 | Clark et al. |
| 5,363,041 A | 11/1994 | Sezginer |
| 5,365,171 A | 11/1994 | Buess et al. |
| 5,376,884 A | 12/1994 | Sezginer |
| 5,379,216 A | 1/1995 | Head |
| 5,381,092 A | 1/1995 | Freedman |
| 5,387,865 A | 2/1995 | Jerosch-Herold et al. |
| 5,389,877 A | 2/1995 | Sezginer et al. |
| 5,397,989 A | 3/1995 | Spraul et al. |
| 5,400,786 A | 3/1995 | Allis |
| 5,412,320 A | 5/1995 | Coates |
| 5,417,104 A | 5/1995 | Wong |
| 5,432,446 A | 7/1995 | Macinnis et al. |
| 5,453,692 A | 9/1995 | Takahashi et al. |
| 5,486,761 A | 1/1996 | Sezginer |
| 5,486,762 A | 1/1996 | Freedman et al. |
| 5,497,087 A | 3/1996 | Vinegar et al. |
| 5,498,960 A | 3/1996 | Vinegar et al. |
| 5,517,115 A | 5/1996 | Prammer |
| 5,536,938 A | 7/1996 | Mills et al. |
| 5,557,200 A | 9/1996 | Coates |
| 5,557,201 A | 9/1996 | Kleinberg et al. |
| 5,557,205 A | 9/1996 | Ohta et al. |
| 5,565,775 A | 10/1996 | Stallmach et al. |
| 5,574,417 A | 11/1996 | Dorri et al. |
| 5,596,274 A | 1/1997 | Sezginer |
| 5,602,334 A | 2/1997 | Proett et al. |
| 5,629,623 A | 5/1997 | Sezginer et al. |
| 5,644,076 A | 7/1997 | Proett et al. |
| 5,644,231 A | 7/1997 | Wignall et al. |
| 5,652,517 A | 7/1997 | Maki et al. |
| 5,672,819 A | 9/1997 | Chin et al. |
| 5,675,147 A | 10/1997 | Ekstrom et al. |
| 5,680,043 A | 10/1997 | Hurlimann et al. |
| 5,696,448 A | 12/1997 | Coates et al. |
| 5,701,112 A | 12/1997 | Brown |
| 5,705,927 A | 1/1998 | Sezginer et al. |
| 5,712,566 A | 1/1998 | Taicher et al. |
| 5,741,962 A | 4/1998 | Birchak et al. |
| 5,757,186 A | 5/1998 | Taicher et al. |
| 5,757,191 A | 5/1998 | Gianzero |
| 5,767,674 A | 6/1998 | Griffin et al. |
| 5,796,252 A | 8/1998 | Kleinberg et al. |
| 5,826,662 A | 10/1998 | Beck et al. |
| 5,828,214 A | 10/1998 | Taicher et al. |
| 5,834,936 A | 11/1998 | Taicher et al. |
| 5,869,755 A | 2/1999 | Ramamoorthy et al. |
| 5,914,598 A | 6/1999 | Sezginer et al. |
| 5,923,167 A | 7/1999 | Chang et al. |
| 5,934,374 A | 8/1999 | Hrametz et al. |
| 5,936,405 A | 8/1999 | Prammer et al. |
| 5,959,453 A | 9/1999 | Taicher et al. |
| 5,977,768 A | 11/1999 | Sezginer et al. |

| | | |
|---|---|---|
| 5,992,519 A | 11/1999 | Ramakrishnan et al. |
| 6,005,389 A | 12/1999 | Prammer |
| 6,008,646 A | 12/1999 | Griffin et al. |
| 6,018,243 A | 1/2000 | Taicher et al. |
| 6,023,163 A | 2/2000 | Flaum et al. |
| 6,023,164 A | 2/2000 | Prammer |
| 6,046,587 A | 4/2000 | King et al. |
| 6,049,205 A | 4/2000 | Taicher et al. |
| 6,051,973 A | 4/2000 | Prammer |
| 6,065,335 A | 5/2000 | Denz et al. |
| 6,065,355 A | 5/2000 | Schultz |
| 6,069,479 A | 5/2000 | Taicher et al. |
| 6,081,116 A | 6/2000 | Wu et al. |
| 6,107,796 A | 8/2000 | Prammer |
| 6,107,797 A | 8/2000 | Sezginer |
| 6,111,408 A | 8/2000 | Blades et al. |
| 6,111,409 A | 8/2000 | Edwards et al. |
| 6,114,851 A | 9/2000 | Kruspe et al. |
| 6,115,671 A | 9/2000 | Fordham et al. |
| 6,118,272 A | 9/2000 | Taicher et al. |
| 6,121,773 A | 9/2000 | Taicher et al. |
| 6,121,774 A | 9/2000 | Sun |
| 6,133,734 A | 10/2000 | McKeon |
| 6,133,735 A | 10/2000 | Hurllmann et al. |
| 6,140,817 A | 10/2000 | Plaum et al. |
| 6,163,154 A | 12/2000 | Anderson et al. |
| 6,166,543 A | 12/2000 | Sezginer et al. |
| 6,173,793 B1 | 1/2001 | Thompson et al. |
| 6,176,323 B1 | 1/2001 | Weirich et al. |
| 6,204,663 B1 | 3/2001 | Prammer |
| 6,216,782 B1 | 4/2001 | Skinner |
| 6,218,833 B1 | 4/2001 | Kruspe et al. |
| 6,229,308 B1 * | 5/2001 | Freedman ................... 324/303 |
| 6,232,778 B1 | 5/2001 | Speier et al. |
| 6,237,404 B1 | 5/2001 | Crary et al. |
| 6,242,912 B1 * | 6/2001 | Prammer et al. ............ 324/303 |
| 6,242,913 B1 | 6/2001 | Prammer |
| 6,246,236 B1 | 6/2001 | Poitzsch et al. |
| 6,252,405 B1 | 6/2001 | Watkins et al. |
| 6,253,155 B1 | 6/2001 | Hagiwara |
| 6,255,817 B1 | 7/2001 | Poitzsch et al. |
| 6,255,818 B1 | 7/2001 | Heaton et al. |
| 6,255,819 B1 | 7/2001 | Day et al. |
| 6,268,726 B1 | 7/2001 | Prammer et al. |
| 6,274,865 B1 | 8/2001 | Schroer et al. |
| 6,297,632 B1 | 10/2001 | Speier |
| 6,301,959 B1 | 10/2001 | Hrametz et al. |
| 6,327,538 B1 | 12/2001 | Chin |
| 6,344,744 B2 | 2/2002 | Taicher et al. |
| 6,346,813 B1 | 2/2002 | Kleinberg |
| 6,362,619 B2 | 3/2002 | Prammer et al. |
| 6,392,409 B1 | 5/2002 | Chen |
| 6,492,809 B1 | 12/2002 | Speier et al. |
| 6,512,371 B2 * | 1/2003 | Prammer ................... 324/303 |
| 6,518,754 B1 | 2/2003 | Edwards |
| 6,518,756 B1 | 2/2003 | Morys et al. |
| 6,518,758 B1 | 2/2003 | Speier et al. |
| 6,525,534 B2 | 2/2003 | Akkurt et al. |
| 6,531,868 B2 | 3/2003 | Prammer |
| 6,541,969 B2 | 4/2003 | Sigal et al. |
| 6,559,640 B2 | 5/2003 | Taicher |
| 6,563,314 B1 | 5/2003 | Kleinberg |
| 6,577,125 B2 | 6/2003 | Prammer et al. |
| 6,583,621 B2 | 6/2003 | Prammer et al. |
| 6,586,931 B2 | 7/2003 | Taicher |
| 6,646,437 B1 | 11/2003 | Chitale et al. |
| 6,661,226 B1 | 12/2003 | Hou et al. |
| 6,688,390 B2 | 2/2004 | Bolze et al. |
| 6,717,404 B2 | 4/2004 | Prammer |
| 6,729,399 B2 | 5/2004 | Follini et al. |
| 6,737,864 B2 * | 5/2004 | Prammer et al. ............ 324/303 |
| 6,748,328 B2 | 6/2004 | Storm, Jr. et al. |
| 6,766,854 B2 | 7/2004 | Ciglenec et al. |
| 6,825,657 B2 | 11/2004 | Kleinberg et al. |
| 6,825,658 B2 * | 11/2004 | Coates et al. ............... 324/303 |
| 6,833,699 B2 | 12/2004 | Galford et al. |
| 6,838,875 B2 | 1/2005 | Freedman |
| 6,859,032 B2 | 2/2005 | Heaton et al. |
| 6,891,369 B2 | 5/2005 | Hurlimann et al. |
| 6,956,371 B2 * | 10/2005 | Prammer ................... 324/303 |
| 6,987,385 B2 * | 1/2006 | Akkurt et al. ............... 324/303 |
| 7,091,719 B2 * | 8/2006 | Freedman ................... 324/303 |
| 7,164,267 B2 * | 1/2007 | Prammer et al. ............ 324/303 |
| 7,199,580 B2 * | 4/2007 | Akkurt ...................... 324/303 |
| 7,463,027 B2 | 12/2008 | Prammer et al. |
| 7,501,818 B2 * | 3/2009 | Akkurt ...................... 324/303 |
| 7,511,487 B2 * | 3/2009 | Badry et al. ................ 324/303 |
| 2002/0163334 A1 | 11/2002 | Hagiwara |
| 2003/0066646 A1 | 4/2003 | Shammai et al. |
| 2003/0094040 A1 | 5/2003 | Proett et al. |
| 2004/0055400 A1 | 3/2004 | Ringgenberg et al. |
| 2007/0241750 A1 | 10/2007 | Akkurt |
| 2009/0058415 A1 * | 3/2009 | Dorovsky et al. .......... 324/303 |

FOREIGN PATENT DOCUMENTS

| | | |
|---|---|---|
| EP | 0 295 134 A2 | 12/1988 |
| EP | 0489578 | 12/1991 |
| EP | 0 581 666 A3 | 2/1994 |
| EP | 0 649 035 B1 | 4/1995 |
| EP | 0 689 722 | 1/1996 |
| GB | 2 056 082 A | 7/1980 |
| GB | 2 310 500 | 8/1997 |
| GB | 2 341 448 A | 3/2000 |
| GB | 2 341 685 A | 3/2000 |
| GB | 2348222 | 9/2000 |
| GB | 2 396 648 A | 6/2004 |
| JP | 404332107 A | 11/1992 |
| JP | 404346089 A | 12/1992 |
| WO | WO 92/10768 | 6/1992 |
| WO | WO 96/12976 | 5/1996 |
| WO | WO 97/14063 | 4/1997 |
| WO | WO 98/25164 | 6/1998 |
| WO | WO 98/29639 | 7/1998 |
| WO | WO 00/14576 | 3/2000 |
| WO | WO 01/42807 | 6/2001 |

OTHER PUBLICATIONS

Akkurt et al., "NMR Logging of Natural Gas Reservoirs," SPWLA 36th Annual Logging Symposium (Jun. 26-29, 1995).

Akkurt et al., "Selection of Optimal Acquisition Parameters for MRIL Logs," SPWLA 37th Annual Logging Symposium, Jun. 16-19, 1996.

Appel et al., "Reservoir fluid study by nuclear magnetic resonance," Paper: SPWLA, presented at the $41^{st}$ Annual Logging Symposium, Jun. 4-27, 2000, Dallas, TX.

Ayan et al., "Measuring Permeability Anisotropy: The Latest Approach", Oilfield Review vol. 6, No. 4, pp. 24-35, Oct. 1994.

Bloembergen et al., "Relaxation effects in nuclear magnetic resonance absorption," Phys Rev, Apr. 1, 1948;73(7):679-712.

Brown et al., "Nuclear Magnetism Logging," Transactions of the American Institute of Mining, Metallurgical, and Petroleum Engineers, vol. 219 (1960), pp. 199-207.

Brown, "Proton relaxation in crude oils," Nature, Feb. 4, 1961;189(4762):387-9.

Brownstein et al., "Importance of classical diffusion in NMR studies of water in biological cells," The American Physical Society, vol. 19, No. 6, (1979) pp. 2446-2453.

Burley et al., IUN/FYDE Introductory Physics Notes, http://theory.uwinnipeg.ca/physics/index.htm, Feb. 5, 1996; specifically . . . /physics/curr/node3.html, . . . /node6.html, and . . . /node7.html.

Cannon et al., "Quantitative NMR Interpretation," Society of Petroleum Engineers, SPE 49010, 1998.

Carr et al., "Effects of Diffusion on Free Precision in Nuclear Magnetic Resonance Experiments," *Physical Review*, vol. 94. No. 3 (May 1, 1954), pp. 630-638.

Chandler et al., "Improved Log Quality with a Dual-Frequency Pulsed NMR Tool," *Society of Petroleum Engineers* (1994) pp. 23-35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Estimation of Hydrocarbon Viscosity with Multiple TE Dual Wait-Time MRIL Logs," Society of Petroleum Engineers, SPE 49009, 1998.

Chen et al., "Improving the Accuracy of NMR Relaxation Distribution Analysis in Clay-Rich Reservoirs and Core Samples," paper SCA 9702, in 1997 international symposium proceedings: Society of Professional Well Log Analysts, Society of Core Analysts Chapter-at-large, p. 10, 1997.

Clavier et al., "Theoretical and Experimental Bases for the Dual-Water Model for Interpretation of Shaly Sands," Society of Petroleum Engineers Journal, 1984, pp. 153-168.

Close et al., "Measurement of BHA Vibration Using MWD," IADC/SPE Drilling Conference, Feb. 28-Mar. 2, 1988.

Coates et al., "A New Approach to Improved Log-Derived Permeability," SPWLA Fourteenth Annual Logging Symposium, May 6-9, 1973, pp. 1-27.

Coates et al., "An Investigation of a New Magnetic Resonance Imaging Log," National SPWLA Convention (Jun. 18, 1991), pp. 1-24.

Coates et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1-15.

Coates et al., "The Magnetic Resonance Imaging Log Characterized by Comparison With Petrophysical Properties and Laboratory Core Data," Society of Petroleum Engineers, SPE 22723, 1991, pp. 627-635.

Davidson et al., Soil Mechanics, http://fbe.uwe.ac.uk/public/geocal/SoilMech/water/water.htm, May 2000.

Delhomme et al., "Permeability and Porosity Upscaling in the Near-Wellbore Domain: The Contribution of Borehole Electrical Images", SPE 36822, Europ. Petrol. Conf. Oct. 22-24, 1996,89-101.

Dunn et al., "A Method for Inverting NMR Data Sets With Different Signal to Noise Ratios," SPWLA 39th Annual Logging Symposium, May 26-29, 1998.

Edwards et al., "Improved NMR Well Logs From Time-Dependent Echo Filtering," SPWLA 37th Annual Logging Symposium, Jun. 16-19, 1996.

Edwards, Carl M., "Effects of Tool Design and Logging Speed on T2 NMR Log Data," SPWLA 38th Annual Logging Symposium, Jun. 15-18, 1997.

Ezzedine et al., "Bayesian Integration of Hydrogeological and Geophysical Data for Site Characterization: Theory and Application to the LLNL Superfund Site", Berkely CA, Mar. 25-28, 2002.

Farrar et al., "Pulse and Fourier Transform NMR Introduction to Theory and Methods," Academic Press (1971) pp. 26-29.

Freedman et al., "Combining NMR and Density Logs for Petrophysical Analysis in Gas-Bearing Formations," SPWLA 39th Annual Logging Symposium, May 26-29, 1998.

Freedman et al., A new NMR method of fluid characterization in reservoir rocks: Experimental confirmation and simulation results, SPE-63214:717-31, Society of Petroleum Engineers Inc., presented at the 75$^{th}$ Annual Technical Conference and Exhibition, Oct. 1-4, 2000, Dallas TX.

Gallegos et al., "A NMR Technique for the Analysis of Pore Structure: Application to Materials with Well-Defined Pore Structure," Journal of Colloid and Interface Science, vol. 119, No. 1, Sep. 1987, pp. 127-140.

Gallegos et al., "A NMR Technique for the Analysis of Pore Structure: Determination of Continuous Pore Size Distributions," Journal of Colloid and Interface Science, vol. 122, No. 1, Mar. 1988, pp. 143-153.

Georgi et al., " On the Relationship between Resistivity and Permeability Anisotropy", SPE 77715, 77th Ann. Techn. Conf. of the SPE, Sep. 29-Oct. 2, 2002 (14 pages).

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore-Size Variations in Reservoir Sandstones," *Society of Petroleum Engineers* (1990), pp. 733-741.

Hull et al., "Field Examples of Nuclear Magnetism Logging," Journal of Petroleum Technology, 1960, pp. 14-22.

Jackson et al., "Western Gas Sands Project Los Alamos NMR Well Logging Tool Development," Los Alamos National Laboratory (Oct. 1981-Sep. 1982) pp. 1-28.

Jackson, Jasper A., "Nuclear Magnetic Resonance Well Logging," The Log Analyst, Sep.-Oct. 1984, pp. 16-30.

Jansen, "Whirl and Chaotic Motion of Stabilized Drill Collars," SEP 20930, Jun. 1992.

Joshi, Horizontal Well Technology, Pennwell Publishing Company, 1991.

Kenyon et al., "Nuclear Magnetic Resonance Imaging—Technology for the 21$^{st}$ Century," Schlumberger Oilfield Review, Autumn 1995.

Kenyon et al., "Pore-Size Distribution and NMR in Microporous Cherty Sandstones," SPWLA Thirtieth Annual Logging Symposium (Jun. 11-14, 1989), pp. 1-24.

Kleinberg et al., "NMR Properties of Reservoir Fluids," The Log Analyst, Nov.-Dec. 1996, pp. 20-32.

Kleinberg et al., "Novel NMR Apparatus for Investigating an External Sample," *Journal of Magnetic Resonance*, (1992) pp. 466-485.

Kleinberg et al., "Nuclear Magnetic Resonance of Rocks: T1 vs. T2," Society of Petroleum Engineers, SPE 26470, 1993, pp. 553-563.

Lindsay et al., "Sequential Backus Averaging: Upscaling well logs to seismic wavelengths", The Leading Edge, vol. 20, Issue 2, pp. 188-191 (Feb. 2001).

Lo et al., "Relaxation time and diffusion measurements of methane and n-decane mixtures," The Log Analyst, Nov.-Dec. 1998;43-7.

Lo et al., Correlations of NMR relaxation time with viscosity, diffusivity, and gas/oil ratio of methane/hydrocarbon mixtures, SPE 63217:757-71, Society of Petroleum Engineers, presented at the 75$^{th}$ Annual Technical Conference and Exhibition, Oct. 1-4, 2000, Dallas, TX.

McKeon et al., "An Improved NMR Tool Design for Faster Logging", SPWLA, 40$^{th}$ Annual Logging Symposium, May-Jun. 1999.

Menger et al., "A New Algorithm for Analysis of NMR Logging Data," Society of Petroleum Engineers, Inc., SPE 49013, 1998.

Mesri et al., "Mechanisms controlling the permeability of clays," Clays and Clay Minerals, 1971, 19:151-158.

Miller et al., "Spin Echo Magnetic Resonance Logging: Porosity and Free Fluid Index Determination," *Society of Petroleum Engineers*, SPE 20561 (1990), pp. 321-334.

Morriss et al., "Field Test of an Experimental Pulsed Nuclear Magnetism Tool," SPWLA Annual Logging Symposium (Jun. 13-16, 1993), pp. 1-23.

Morriss et al., "Hydrocarbon Saturation and Viscosity Estimation from NMR Logging in the Belridge Diatomite," 35th SPWLA Annual Logging Symposium (Jun. 19-22, 1994), pp. 1-24.

Moulton et al., "Multilevel upscaling in heterogeneous porous media", Research Highlights LA-UR 99-4754, Center for Nonlinear Studies, Los Alamos National Laboratory, Jan. 1999.

Nascimento et al., "Anomalous NMR Responses in Highly Permeable Sandstone Reservoirs: A Case Study," SPWLA 40th Annual Logging Symposium, May 30-Jun. 3, 1999.

Nelson, "Permeability-porosity relationships in sedimentary rocks," The Log Analyst, May-Jun. 1994, 38-62.

Neuman et al., "Applications of Nuclear Magnetism Logging to Formation Evaluation," Journal of Petroleum Technology, vol. 34, (1982) pp. 2853-2862.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195-260.

Prammer et al., "A New Multiband Generation of NMR Logging Tools," Society of Petroleum Engineers, SPE 49011, 1998.

Prammer et al., "Measurements of Clay-Bound Water and Total Porosity by Magnetic Resonance Logging," Society of Petroleum Engineers, SPE 36522, 1996.

Prammer et al., "Theory and Operation of a New, Multi-Volume, NMR Logging System," SPWLA 40th Annual Logging Symposium, May 30-Jun. 3, 1999.

Prammer, et al., "Lithology-Independent Gas Detection by Gradient NMR Logging," Society of Petroleum Engineers, paper SPE-30562, published in the transactions to the 1995 SPE Annual Technical Conference & Exhibition, pp. 325-336.

Prammer, M.G., "NMR Pore Size Distributions and Permeability at the Well Site," *Society of Petroleum Engineers*, SPE 28368, (1994) pp. 55-64.

Proett et al., "New wireline formation testing tool with advanced sampling technology," SPE 56711:483-98, Society of Petroleum Engineers Inc., presented at the $74^{th}$ Annual Technical Conference and Exhibition, Oct. 3-6, 1999, Houston, TX.

Revil et al., "Permeability of shaly sands," Water Resources Research, Mar. 1999, 35(3): 651-662.

*Schlumberger Wireline & Testing*, "Combinable Magnetic Resonance tool reliably indicates water-free production and reveals hard-to-find pay zones," (Jun. 1995).

Setser et al., "Measurement of Remaining Oil Saturation in Northern Michigan Using Nuclear Magnetism Log Data and Pressure Core," Society of Petroleum Engineers, SPE 14276, 1985.

Singer et al., "Fast NMR Logging for Bound Fluid and Permeability," SPWLA 38th Annual Logging Symposium, Jun. 15-18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40-56.

Tabanou et al., "Thinly laminated reservoir evaluation in oil-base mud: High resolution versus bulk anisotropy measurement—a comprehensive evaluation," SPWLA $43^{rd}$ Ann. Logging Symp. (14 pages).

Tang et al., "LP-ZOOM, a Linear Prediction Method for Local Spectral Analysis of NMR Signals," Journal of Magnetic Resonance 79, 190-196 (1988).

The Mathworks, Inc., Image Processing Toolbox for Use with MATLAB, User's Guide, Version 2, May 1997.

Van Baaren, "Quick-look permeability estimates using sidewall samples and porosity logs," 6th Ann. European Logging Symp. Transactions, SPWLA, 1979.

Van Dussen et al., "Determination of hydrocarbon properties by optical analysis during wireline fluid sampling," SPE-63252:773-85, Society of Petroleum Engineers Inc., presented at the $75^{th}$ Annual Technical Conference and Exhibition, Oct. 1-4, 2000, Dallas, TX.

Vernik, "Permeability Prediction in Poorly Consolidated Siliciclastics Based on Porosity and Clay Volume Logs," Petrophysics, Mar.-Apr. 2000, 138-147.

Waxman et al., "Electrical Conductivities in Oil-Bearing Shaly Sands," *Society of Petroleum Engineers Journal* (1968) pp. 107-122.

Witt et al., A comparison of wireline and drillstern test fluid samples from a deepwater gas-condensate exploration well, SPE 56714, 1999 SPE Ann. Tech. Conf. and Exhibit., Oct. 3-6, 1999, 515-524.

Wu et al., "Inversion of multi-phase petrophysical properties using pumpout sampling data acquired with a wireline formation tester, " SPE 77345, 2002 (16 pages).

Xian Huan-Wen et al., "Upscaling hydraulic conductivities in heterogenous media: an overview", J. Hydrology 183 (1996) pp. ix-xxxii.

Zhang et al., "Some exceptions to default NMR rock and fluid properties," SPWLA:1-14, presented at the $39^{th}$ Annual Logging Syposium, May 26-29, 1998, Keystone, CO.

Great Britan Examination Report for Application No. GB0504935.8 dated Jun. 21, 2005.

Great Britan Examination Report for Application No. GB0606829.0 dated Sep. 8, 2006.

PCT International Preliminary Report on Patentability in Int'l Application No. PCT/US2005/000162 dated Jul. 10, 2006.

PCT International Search Report in Int'l Application No. PCT/US2004/32335 dated Aug. 29, 2005.

PCT International Preliminary Report on Patentability in Int'l Application No. PCT/US2004/32335 dated Apr. 10, 2006.

Suppl. Partial European Search Report in European Application No. 04718003.9-2315 dated Apr. 13, 2006.

Suppl. European Search Report in European Application No. 04718003.9-2315 dated Oct. 25, 2006.

PCT International Search Report for Int'l Application No. PCT/US2004/006784 dated Nov. 29, 2004.

PCT International Preliminary Report on Patentability in Int'l Application No. PCT/US2004/006784 dated Sep. 9, 2005.

PCT International Search Report for Int'l Application No. PCT/US2004/43437 dated Nov. 2, 2005.

PCT International Preliminary Report on Patentability in Int'l Application No. PCT/US2004/43437 dated Jun. 26, 2006.

EPO Supplementary European Search Report EP 02 72 5424 dated Jun. 8, 2004.

EPO Communication Pursuant to Article 92(2) EPC EP 02725424.2 dated Jan. 25, 2005.

EPO Communication Pursuant to Article 92(2) EPC EP 02725424.2 dated Oct. 12, 2005.

International Search Report PCT/US02/09819 dated Jul. 12, 2002.

International Preliminary Examination Report PCT/US02/09819 dated Nov. 15, 2002.

European Search Report for application No. 03791853.9-1234, dated Oct. 8, 2009.

Norwegian Search Report for application No. 20003266, dated Nov. 11, 2009.

Norwegian Search Report for application No. 20003622, dated Jan. 14, 2010.

Notice of Allowance for U.S. U.S. Appl. No. 12/261,343, Jan. 11, 2009.

* cited by examiner

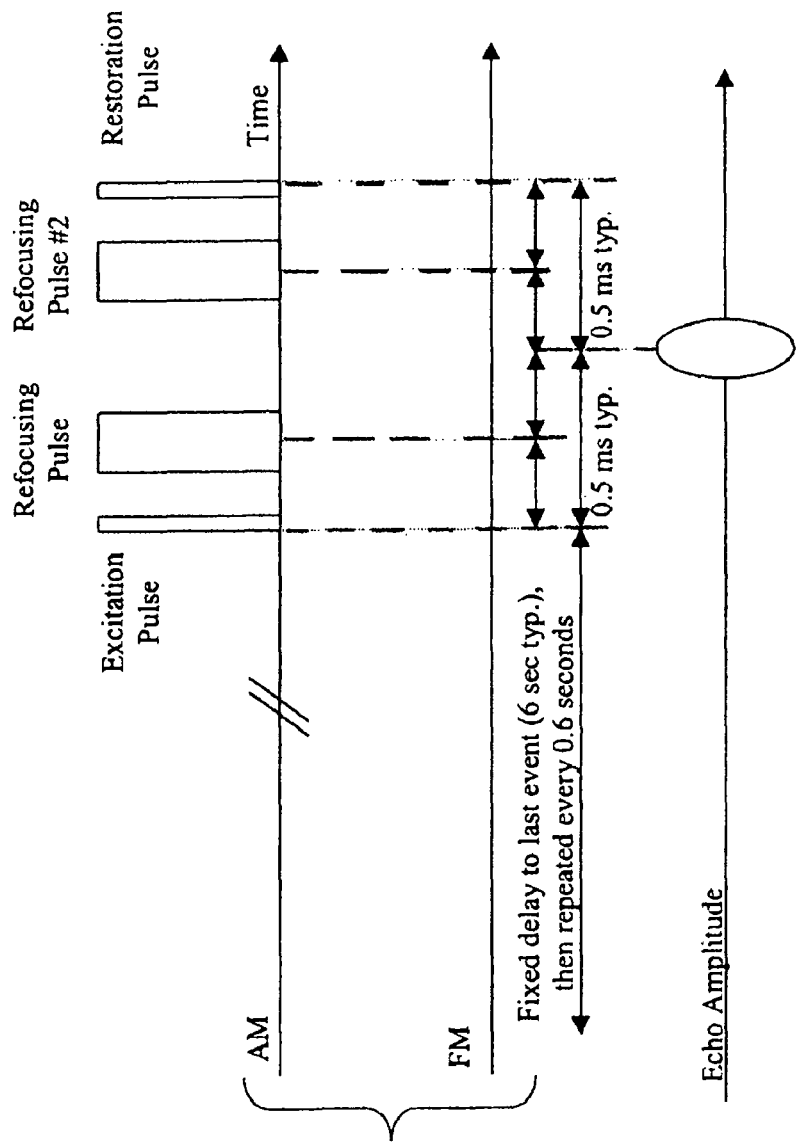
Fig. 4
REPLACEMENT SHEET

SYSTEM AND METHODS FOR T1-BASED LOGGING

CROSS-REFERENCE TO RELATED APPLICATIONS

This patent application is a division of U.S. patent application Ser. No. 11/731,121, filed on Mar. 29, 2007 now U.S. Pat. No. 7,501,818, which is a division of U.S. patent application Ser. No. 10/957,406, filed on Oct. 1, 2004 now U.S. Pat. No. 7,199,580, which claims the benefit of the Oct. 3, 2003 filing date of U.S. provisional patent application No. 60/508,442.

FIELD OF THE INVENTION

The present invention relates generally to nuclear magnetic resonance (NMR) well logging and in particular to $T_1$ relaxation measurements for wireline, logging-while-drilling (LWD) and other applications.

BACKGROUND OF THE INVENTION

In oil and gas exploration it is desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) or measurement-while-drilling (MWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

NMR logging has become very important for purposes of formation evaluation and is one of the preferred methods for determining formation parameters because of its non-destructive character. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest. In general, NMR logging devices may be separate from the drilling apparatus (in what is known as wireline logging), or they may be lowered into the borehole along with the drilling apparatus, enabling NMR measurement while drilling is taking place. The latter types of tools are known in the art as logging-while-drilling (LWD) or measurement-while-drilling (MWD) logging tools NMR tools used in practical applications include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23-26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25-28, 1994.

Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448; 5,936,405; 6,005,389; 6,023,164; 6,051,973; 6,107,796; 6,111,408; 6,242,913; 6,255,819; 6,268,726; 6,362,619; 6,512,371; 6,525,534; 6,531,868; 6,541,969; 6,577,125 and 6,583,621. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466-485, 1992; and "An Improved NMR Tool Design for Faster Logging," D. McKeon et al., SPWLA 40th Annual Logging Symposium, May-June 1999. The content of the above patents is hereby expressly incorporated by reference for all purposes, and all non-patent references are incorporated by reference for background.

NMR logging is based on the observation that when an assembly of magnetic moments, such as those of hydrogen nuclei, are exposed to a static magnetic field, they tend to align along the direction of the magnetic field, resulting in bulk magnetization. The rate at which equilibrium is established in such bulk magnetization is characterized by the parameter $T_1$, known as the spin-lattice relaxation time. The $T_1$ parameter characterizes the coupling of nuclear spins to energy-absorbing molecular motions like rotation, vibration and translation.

Another related and frequently used NMR logging parameter is the spin-spin relaxation time $T_2$ (also known as transverse relaxation time), which is an expression of the relaxation due to non-homogeneities in the local magnetic field over the sensing volume of the logging tool. In general, the mechanisms for spin-spin relaxation time $T_2$ include, in addition to those contributing to $T_1$, the exchange of energy between spins. Both the $T_1$ and the $T_2$ relaxation times provide information about formation porosity, composition and quantity of formation fluid, and other parameters important in oil exploration.

The pioneers in NMR measurement technologies envisioned the relaxation time $T_1$ as the primary measurement result because it carries only information about the liquid-solid surface relaxation and bulk-fluid relaxation. In particular, unlike the transverse relaxation time $T_2$, the spin lattice relaxation parameter $T_1$ is not affected by rock-internal magnetic field gradients or by differences in fluid diffusivity. Moreover, instrument artifacts influence $T_1$ measurements to a much lesser degree than $T_2$ measurements.

Despite this understanding, modern pulsed NMR logging in the early 1990s was based primarily on $T_2$ measurements, largely because of hardware limitations. Specifically, the construction of the $T_1$ recovery curve requires data collected with multiple wait times that range from a few milliseconds to several seconds. Acquiring $T_1$ data using tools that operated in single-frequency mode without effective pre-polarization was too time-consuming and not feasible. $T_2$ measurements, on the other hand, were faster and contained information similar to $T_1$ at low resonance frequencies. As a result, $T_2$ CPMG measurements were chosen as the main mode of tool operation.

One characteristic of NMR logging is that unlike many other logging methods the measurements are not instantaneous. Each measurement cycle, including the wait time needed for polarization, can take several seconds. Frequently, several cycles have to be stacked to achieve adequate signal-to-noise ratio (SNR).

Thus, if a cycle takes T seconds to complete, and N cycles must be stacked, the vertical resolution of a measurement is inversely proportional to vNT, where v is the logging speed. Clearly, the longer the cycle times and the higher the logging speeds, the worse the vertical resolution. Therefore, an ever-present challenge in NMR logging is to design tools that can log faster, while retaining acceptable vertical resolution. For practical reasons overcoming this challenge is a important task. Several innovations towards faster logging have been put into practice over the past several years.

One such innovation was the introduction of multi-frequency logging in the early 1990s. The benefit of multi-frequency logging is that the tools acquire data simultaneously over several frequencies, and the additional SNR available can be used to speed up logging as well as to obtain higher-quality results. The state-of-the-art in multi-frequency logging is the MRIL®-Prime tool by Numar, a Halliburton Corporation, which currently can operate on 9 frequencies.

Another innovation was the introduction of simultaneous acquisition of partially and fully polarized echo trains with different SNR. Proper total porosity measurements require: (1) a short interecho time $T_e$ to sample fast decays, (2) high SNR to reduce the uncertainty in the estimation of fast decays, (3) long sampling time ($N_e T_e$ where $N_e$ is the number of echoes) for adequate sampling of longer decays. It is practically impossible to achieve all these objectives with a unique wait time $T_w$, $T_e$ and $N_e$ combination; while maintaining acceptable logging speeds and vertical resolution. Therefore, one solution is to optimize the acquisition by mixing partially and fully recovered data with different measurement parameters $T_w$, $T_e$, $N_e$ and desired SNR. Another closely related innovation was the concept of simultaneous-inversion, where data acquired with different measurement parameters is inverted simultaneously using forward models that properly account for the differences in fluid NMR properties, acquisition parameters and noise levels.

Yet another innovation was the use of pre-polarization. In this approach the cycle time for each measurement is shortened, by placing static magnets above the antenna section to realize additional polarization during tool motion. Current generation NMR tools generally contain pre-polarization sections, allowing overall faster logging. Various other approaches have been attempted in the art, including the patents listed above.

The focus of this application is on novel systems and methods for $T_1$ NMR logging alone or in combination other logging techniques. As discussed in application Ser. No. 60/474, 747, filed on May 03, 2003, to the same assignee as the present application, $T_1$ logging adds a different dimension to interpretation, sometimes by complementing $T_2$ logs, sometimes uniquely by itself. The '747 application is incorporated herein for all purposes. The novel technical approaches in accordance with the present invention directed to overcoming problems associated with the prior art are discussed below.

SUMMARY OF THE INVENTION

In accordance with the present invention systems and methods for using nuclear magnetic resonance (NMR) $T_1$ measurements for wireline, LWD and MWD applications and down-hole NMR fluid analyzers are provided. The $T_1$ measurements are characterized by insensitivity to motion, as the detrimental effects arising from tool motion or fluid flow are effectively reduced or eliminated. $T_1$ measurements alone or in combination with other standard oil field measurements are shown to provide efficient data acquisition resulting in compact and robust data sets, the potential for substantially increased logging speeds, and simple methods for fluid typing, including direct and robust identification of gas.

In one aspect, the present application concerns a direct and more robust method for identification of gas. The method is particularly applicable in tight reservoirs, where the longest $T_1$ for the water phase is known a priori. A simple correction for gas is made possible in such applications, without having to resort to sophisticated processing techniques.

In another aspect, this application concerns ability to use NMR logs with short wait times, on the order of 2 to 3 seconds, capable of determine total porosity estimates using a self-sufficient correction algorithm that provides compensation for insufficient polarization. A particularly important result of this approach is the ability to provide overall faster logging, due to shorter cycle times, or higher vertical resolution, dependent on the practical application. Thus, in a specific embodiment using pre-polarization of the NMR logging tool, good vertical resolution can be provided at logging speeds about or higher than 15 feet per minute.

In particular, in one aspect the invention is directed to a method for identifying gas in a geologic formation, comprising the steps of: providing a distribution of nuclear magnetic resonance (NMR) $T_1$ relaxation times corresponding to a NMR log of the geologic formation; selecting a threshold value in the provided $T_1$ distribution; and integrating the $T_1$ distribution above the selected threshold value to obtain an estimate of gas-filled porosity in the geologic formation.

In another aspect, this application is directed to novel combinations of $T_1$ and $T_2$ logs, for example, to estimate the diffusivity of low viscosity light hydrocarbon (non wetting phase), and combine the above diffusivity estimates to calculate viscosity, and combine the $T_1$ and D) values to estimate gas to oil ratios (GOR).

In yet another aspect, the invention is directed to providing a correction for insufficient polarization of NMR $T_1$ and $T_2$ logs based solely on a distribution of NMR $T_1$ relaxation times and acquisition parameters of the NMR log. In another aspect, the invention is directed to increased-speed $T_1$ logging, based on corrections for pre-polarization magnetization.

BRIEF DESCRIPTION OF THE DRAWINGS

Other objects and many attendant features of this invention will be appreciated and better understood with reference to the following detailed description when considered in connection with the accompanying drawings, wherein:

FIGS. 3 and 4 illustrate pulse sequences that can be used in specific embodiments of the present invention;

DETAILED DESCRIPTION

Theoretical Background

Figure 1:
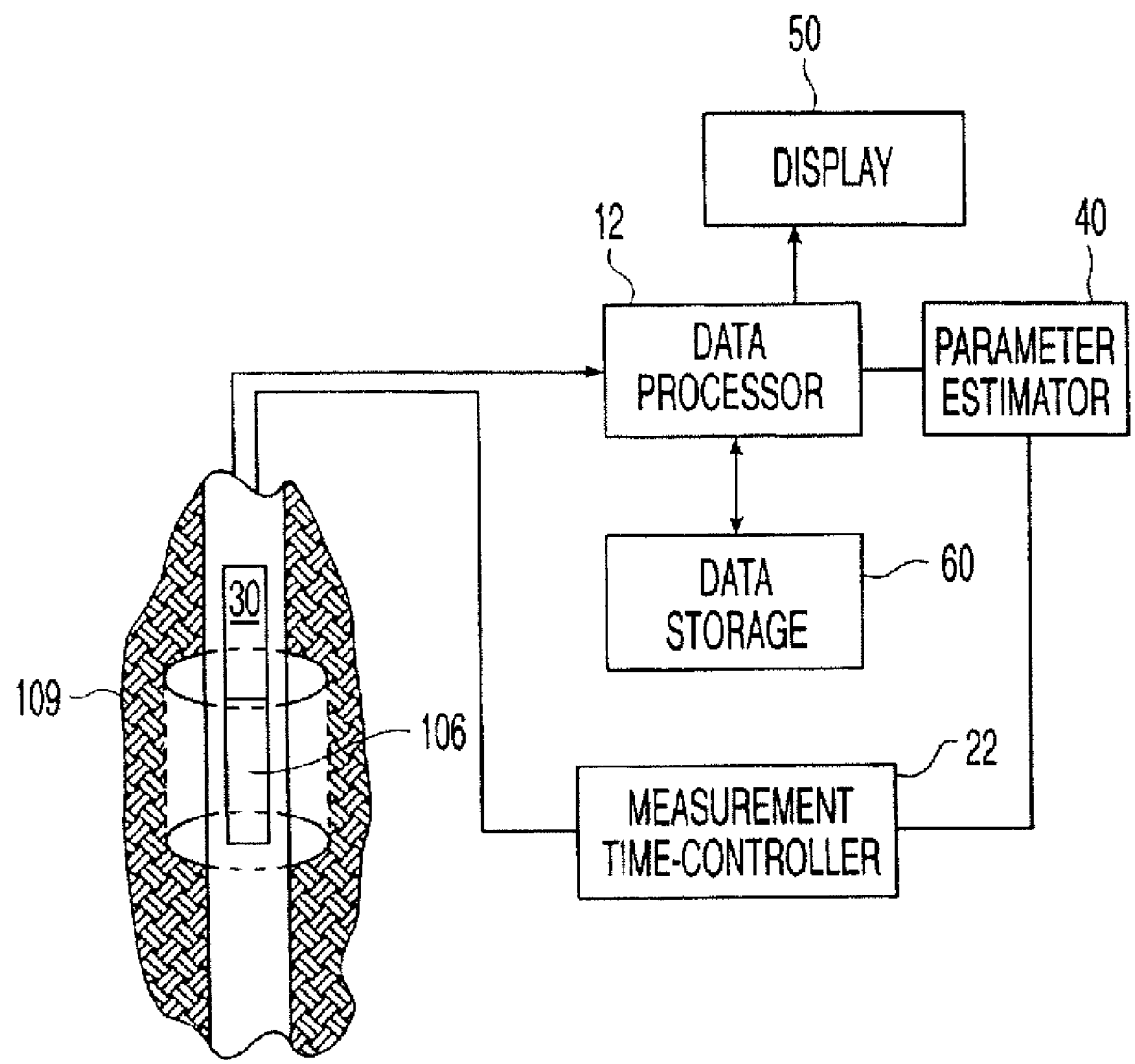
FIG. 1 is a block diagram of a NMR logging system, which can be programmed for use in accordance with a specific embodiment of the present invention.

The first step in any NMR measurement is to align the magnetic nuclei with a magnetic field. This alignment process, or polarization, is not instantaneous and takes some time, which is associated with the $T_1$ parameter. In reservoir rocks, the value of $T_1$ depends on the characteristics of the fluids and the confining pore space. Two distinct relaxation mechanisms acting in parallel determine the longitudinal relaxation time:

$$\frac{1}{T_1} = \frac{1}{T_{1B}} + \frac{1}{T_{1S}} \quad (1)$$

where the subscripts B and S correspond to bulk and surface relaxation, respectively.

Direct measurement of the longitudinal magnetization is not feasible and therefore requires tipping of the spins onto the transverse plane. Relaxation in the transverse plane is generally a more complex process compared to $T_1$ relaxation. In general, the transverse relaxation time $T_2$ is equal to or shorter than its longitudinal counterpart $T_1$. This is mostly due to molecular diffusion characterized by $T_{2D}$, resulting in the following equation for the measured $T_2$ response:

$$\frac{1}{T_2} = \frac{1}{T_{2B}} + \frac{1}{T_{2S}} + \frac{1}{T_{2D}} \quad (2)$$

where the extra term containing the subscript D corresponds to diffusion. Given the typical magnetic field gradients of modern logging tools, diffusion can dominate transverse relaxation in the case of highly diffusive fluids, leading to large $T_1/T_2$ ratios.

Tipping of the spins onto the transverse plane is accomplished through the application of an RF-pulse at a specific resonance frequency (Larmor frequency). Once in the transverse plane, the tipped protons induce a rapidly decaying signal in the receiver coils of the NMR device. The time constant associated with this so-called Free Induction Decay (FID) is on the order of a few tens of microseconds only, making it hard to measure directly. Laboratory measurements that aim at quantifying $T_1$ through Saturation Recovery (SR) or Inversion Recovery (IR), often measure (the amplitude of) this FID. FID measurements have yet to be demonstrated in oil-field logging tools; measurement of $T_1$ or $T_2$ in the field is usually achieved through a series of spin-echo sequences. The best known spin-echo sequence is by Carr, Purcell, Meiboom and Gill (CPMG) and has been developed to facilitate easy measurement of the transverse relaxation time $T_2$.

Although Inversion Recovery is the most popular $T_1$ measurement method in laboratory applications, Saturation Recovery technique is the practical choice in well logging due to its efficiency and shorter cycle times. The SR sequence used for wireline $T_1$ logging can be considered as a series of CPMG echo trainlets, comprised of a few echoes with distinctly different wait times. Within this analogy, the signal from the jth echo of the ith wait time, given relaxation times $T_{1k}$ and $T_{2k}$ with associated amplitudes ak, is given by $$y_{ij} = \sum_{k=1}^{K} a_k (1 - e^{-T_{wi}/T_{1k}}) e^{-jT_e/T_{2k}} \quad (3)$$

where Te is the inter-echo time. Note that the response $y_{ij}$ is dependent on both $T_1$ and $T_2$, and the imprint of $T_2$ is eliminated when j=0. In practice, the decoupling of the $T_2$ response is accomplished by using very short Te, and only a few echoes. Proper sampling in $T_1$ acquisition requires at least a couple of recovery measurements per decade. As a rule of thumb, components faster than the shortest recovery time, or components slower than the longest recovery time can not be resolved. In the example logs shown below, the wait times vary from 10 ms to 6.3 s. The shortest inter-echo time is either 0.51 ms, or 0.60 ms. A maximum of 10 echoes are acquired within each trainlet.

$T_1$ inversion used here is cast as a classic linear least squares problem, where the minimum of an objective function is sought, as described below. By defining the residual or the misfit between the data and the fit by $$\varepsilon_{ij} = d_{ij} - y_{ij} \quad (4A)$$

where $$y_{ij} = \sum_{k=1} x_k (1 - e^{-T_{wi}/T_{1k}}) e^{-jT_e/T_{2k}} \quad (4B)$$

and $d_{ij}$ is the amplitude of the jth echo in the ith CPMG trainlet, the objective function to be minimized to determine that unknown vector x is given by $$\Phi(x) = \sum_{i=1}^{I} \sum_{j=1}^{J} \varepsilon_{ij}^2 + \alpha \sum_{k=1}^{K} x^2 \quad (5)$$

Note that the elements of the unknown vector x contain the amplitudes of the $T_1$ distribution. While the first term in the objective function represents the sum of the squares of the misfit, the second term represents the penalty, or the regularization term that is applied to prevent spiky or oscillatory distributions. Zeroth order regularization has been used in the above equation only for sake of simplicity, since many alternatives exist for regularization. It should be noted here that as part of solving the linear problem, the relaxation times $T_{1k}$ and $T_{2k}$ are determined apriori. However, the longitudinal and transverse relaxation times can not be treated as independent properties since in general $$T_{2k}=f(T_{1k}),\qquad(6)$$

where the explicit dependence may vary with k. The relationship is governed by the relaxivity of the rocks in the case of the wetting phase, and the bulk and diffusivity properties of the fluids in the case of the non-wetting phase.

Other factors such as internal gradients may also come into play in certain cases. In the simplest approach, one can define a linear relationship in the following form $$T_{2k}=T_{1k}/\lambda.\qquad(7)$$

where $\lambda$ is a constant, referred to as the $T_1/T_2$ ratio, with a typical value of 1.5 to 3.0. Actually, the first step of the inversion process used here involves the determination of the function that relates $T_2$ to $T_1$, using a model where the relationship is allowed to be non-linear. The information obtained from this initial process is then used in the inversion to set $T_{2k}$ for a given $T_{1k}$.

Various techniques for $T_1$ and $T_2$ measurements including pulse sequences have been developed in the art, including, without limitation, the disclosures in U.S. Pat. Nos. 5,309, 098; 5,517,115, 5,696,448; 5,936,405; 6,005,389; 6,023,164; 6,049,205; 6,051,973; 6,107,796; 6,111,408; 6,242,913; 6,255,819; 6,268,726; 6,362,619; 6,512,371; 6,525,534; 6,531,868; 6,541,969; 6,577,125; 6,600,316, which are incorporated herein for all purposes.

The System and Underlying Measurements

FIG. 1 is a block diagram of a system, which can be programmed for use in accordance with a specific embodiment of the present invention, which shows individual block components for controlling data collection, processing of the collected data and displaying the measurement results. In FIG. 1 a logging tool 106 comprises an NMR probe controller 30 and pulse echo detection electronics and is lowered in a borehole drilled in the formation 109. The output signal from the tool detection electronics is processed by data processor 12 to record NMR pulse echo data from the tool and analyze the relaxation characteristics of the materials surrounding the borehole. The output of the data processor 12 is fed to parameter estimator 40. Measurement cycle controller 22 provides an appropriate control signals to the probe. The processed data from the log measurements is stored in data storage 60. Data processor 12 is connected to display 50, which is capable of providing a graphical display of one or more measurement parameters, preferably superimposed on display data from data storage 60. The components of the system of the present invention shown in FIG. 1 can be implemented in hardware or software, or any combination thereof suitable for practical purposes.

Figure 2:
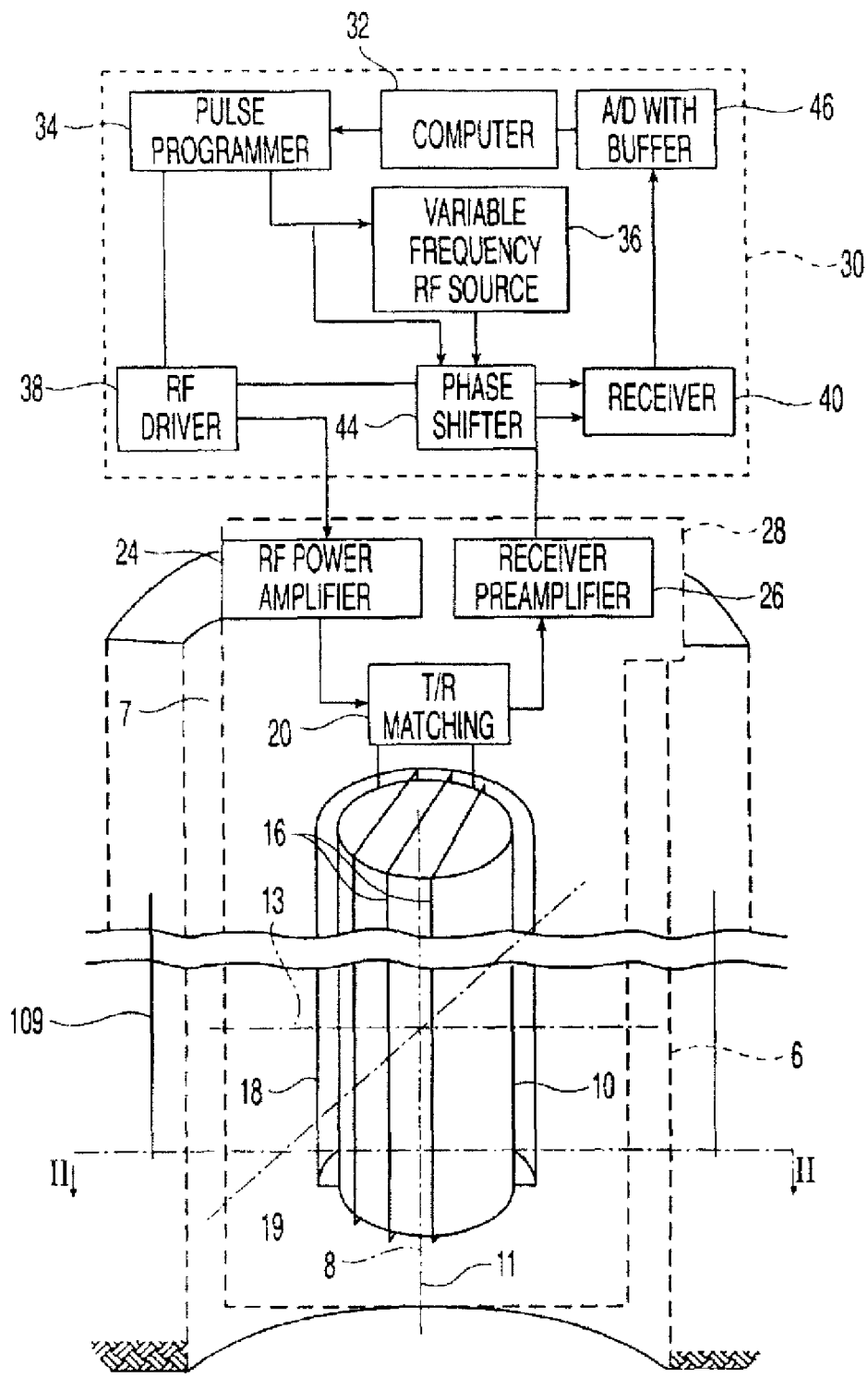
FIG. 2 is a partially schematic, partially block diagram of a NMR logging tool and attached electronics used in one embodiment directed to wireline logging.

Reference is now made to FIG. 2, which illustrates in a semi-block diagram form an NMR logging apparatus, such as the MRIL®-Prime tool of Numar Corporation (a Halliburton Company), which can be used for NMR measurements in accordance with a preferred embodiment of the present invention. In standard operation, first portion 6 of the tool is arranged to be lowered into a borehole 7 having a borehole longitudinal axis 8 in order to examine properties of the geologic formation in the vicinity of borehole 7.

The first portion comprises a generally cylindrical permanent magnet 10, preferably having a longitudinal axis 11, which is preferably coaxial with the longitudinal axis 8 of the borehole. Alternatively, a plurality of permanent magnets 10 may be employed. Permanent magnet 10 preferably has uniform magnetization substantially perpendicular to the longitudinal axis of the logging tool, which is parallel to the longitudinal axis 8 of the borehole 7.

The first portion 6 also comprises one or more coil windings 16, which preferably are arranged on top of the permanent magnet and form the tool antenna. The magnetization direction 13 created by the antenna is substantially perpendicular to the longitudinal axis 11 of the bore hole. The coil windings 16, together with a transmitter/receiver (T/R) matching circuit 20 define a transmitter/receiver (T/R) circuit. T/R matching circuit 20 typically includes a resonance capacitor, a T/R switch and both to-transmitter and to-receiver matching circuitry and is coupled to a first RF power amplifier 24 and to a receiver pre-amplifier 26.

The permanent magnet 10 and coil windings 16 are preferably housed in a non-conductive, non-ferromagnetic protective housing 18. The housing and its contents will hereinafter be referred to as the probe 19. In operation, the probe along with RF amplifier 24, preamplifier 26 and T/R matching circuit 20, designated collectively as housing 28 are passed through the borehole. Alternatively, some of the above elements may be located above ground in housing 30.

Disposed in a housing indicated in FIG. 2 by block 30, is a control circuitry, including a computer 32, which provides a control output to a pulse programmer 34. Pulse programmer 34 controls the operation of phase shifter 44, as well as an RF driver 38, which drives RF power amplifier 24. Pulse programmer 34 controls the operation of a variable frequency RF source 36, the output of which is passed through phase shifter 44 to the RF driver 38. The signal from RF driver 38 is amplified in RF power amplifier 24 and passed through T/R matching circuit 20 to the antenna 16.

NMR signals from excited nuclei in the formation surrounding the borehole are picked up by the receiving antenna 16 and passed through T/R matching circuit 20 to RF receiver pre-amplifier 26, the output of which is supplied to an RF receiver 40 which also receives an input from phase shifter 44. Receiver 40 outputs via an A/D converter with a buffer 46 to the computer 32 for providing desired well logging output data for further use and analysis.

While the above description was provided with reference to wireline logging, it will be apparent that the $T_1$ measurement principles of the present invention in a preferred embodiment can be applied to logging-while-drilling (LWD) or measurement-while-drilling (MWD). Further details on the structure of NMR wireline and LWD tools and fluid analyzers that can be used in accordance with preferred embodiments of the present invention can be found, for example, in U.S. Pat. Nos. 4,710,713; 4,717,876; 4,717,877; 4,717,878; 5,280,243; 5,712,566; 6,023,164; 6,107,796; 6,111,408; 6,268,726; 6,362,619; 6,512,371; 6,525,534; 6,531,868; 6,541,969; 6,577,125 and 6,583,621. Additional designs, as shown in U.S. Pat. Nos. 4,939,648; 5,055,787 and 5,055,788 can also be used. As noted earlier, the above patents have been incorporated herein by reference for all purposes.

In different embodiments, the $T_1$ and $T_2$ measurements in accordance with this invention can be obtained either simultaneously or separately, using the same or different NMR logging tools. In one embodiment, the $T_1$ and $T_2$ measurements are obtained using the LWD-MWD tool disclosed in U.S. Pat. No. 6,531,868, which has been incorporated by reference. Such a tool contains two distinct operating modes, one designed for while-drilling operations and the other for wiping trips. In one embodiment, the motion-tolerant $T_1$ measurements are obtained when drilling motion is detected and the tool switches over to $T_2$ once drilling ceases. In another embodiment, $T_1$ and $T_2$ measurements are acquired simultaneously over the same depth interval during a wiping trip.

In one embodiment, the process for obtaining $T_1$ measurements during a drilling operation is described as follows. At the start of a measurement, one or more radio frequency pulses covering a relatively wide range of frequencies, or using one or more pulses which are frequency swept, are transmitted to saturate the nuclear magnetization in a cylindrical volume around the drilling tool. The range of frequencies can be, for example, 50-100 kHz and is covered in a specific embodiment using a rapid succession of short radio frequency pulses similar to the first pulse in a standard CPMG pulse sequence, or using a single long pulse in a frequency sweep. Changing the range of frequencies used in this step varies the position and the width of the sensitive region in the formation. In a specific embodiment using the tool, a frequency range between 50 and 100 kHz saturates the nuclear magnetization in a cylindrical volume around the tool, where the cylinder has a typical diameter of 14", a height of 24", and thickness of between about 1/2" to 1".

Figure 3:
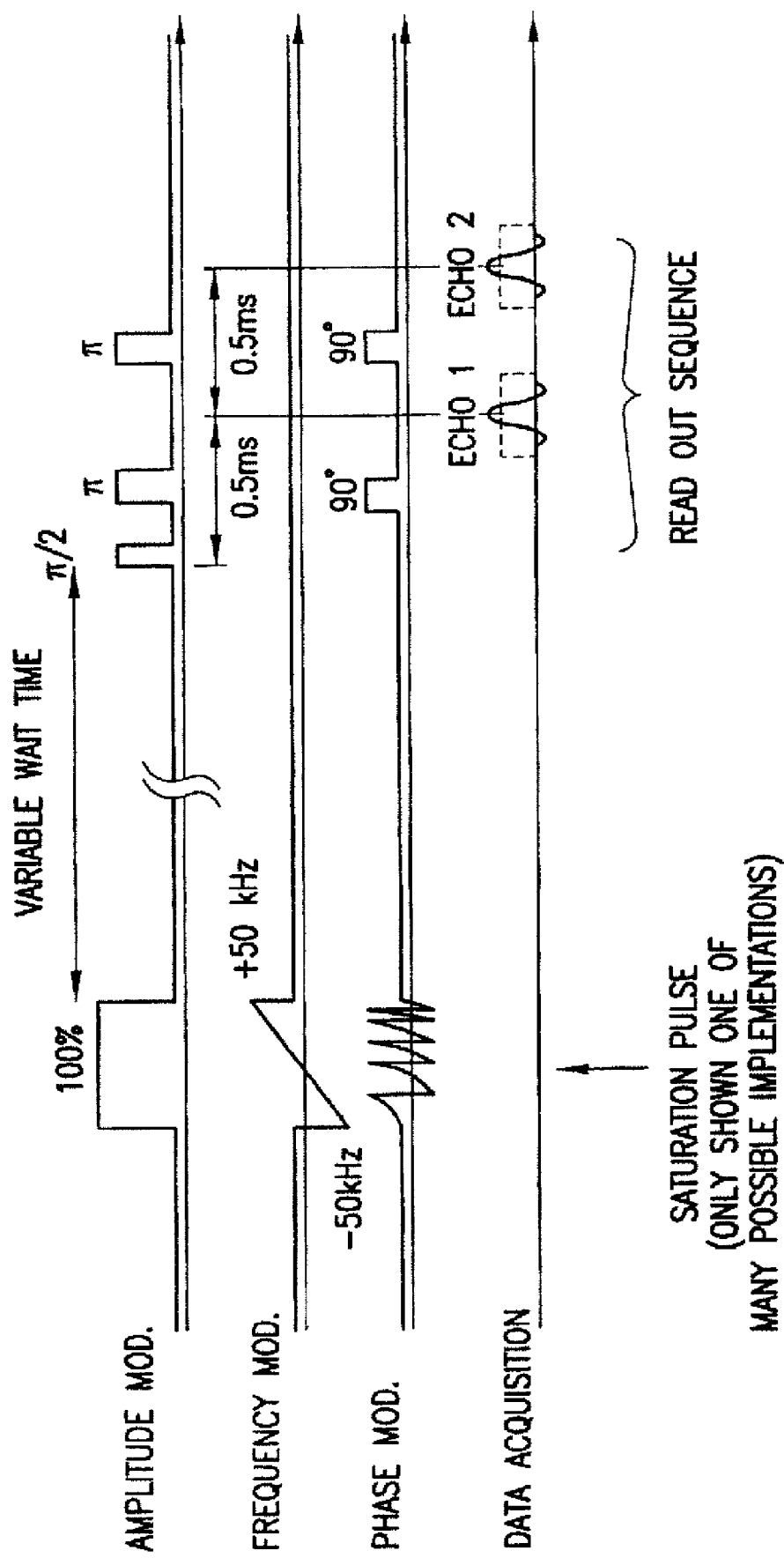

Following the step of saturation, which typically takes about 1 ms, in accordance with the present invention a readout pulse is transmitted at a frequency near the center of the range of covered frequencies. In alternative embodiments one or more subsequent readout pulses can also be used. In accordance with the present invention, a readout pulse sequence is comprised of a 90° pulse followed by data acquisition, or of a 90° pulse followed by a 180° pulse, followed by data acquisition, where the steps of applying a 180° pulse and data acquisition can be repeated. The readout pulse sequence generally follows a predetermined wait time, as explained in more detail below. In a specific embodiment the readout pulse sequence is transmitted at a center frequency of about 500 kHz, and is followed by one or more refocusing pulses. An illustration of a pulse sequence used in a specific embodiment of the present invention is shown in FIG. 3. Yet another type of pulse sequence that can be used in accordance with this invention is illustrated in FIG. 4, as discussed in more detail in the 6,531,868 patent.

Following the readout pulse(s), corresponding NMR echo signals are received, amplified and stored for further processing. In accordance with a preferred embodiment, the amplitude of the retained echo signal is interpreted as the level of nuclear magnetization present after the particular wait time. In the particular example considered above, the center frequency of the NMR echo signals corresponds to about 14" diameter of investigation.

The measurement process described above is repeated for a series of increasing wait times the values of which can, for example, be equally distributed on a logarithmic scale. In a specific embodiment, wait times are stepped through the values 1 ms, 3 ms, 10 ms, 30 ms, 100 ms, 300 ms, 1000 ms and 3000 ms, and the measurement results are stacked to produce several data points on a multi-component $T_1$ relaxation curve. In one embodiment, only a few echoes are collected for each wait time to compute the $T_1$ relaxation curve. Preferably, about two to five echoes per wait time are retained.

$T_2$ measurements can be obtained either separately or simultaneously with $T_1$ measurements. In one embodiment, $T_2$ measurements are obtained simultaneously with $T_1$ measurements during one of the long wait times. This is done by acquiring a large number of echoes, preferably 500, during the long wait time and then using the large number of echoes to compute the $T_2$ relaxation curve.

The $T_1$ and $T_2$ measurements obtained during the drilling operation are processed to derive petrophysical properties of local geological formations. As known in the art, these measurements can be used to compute distributions of $T_1$ and $T_2$ relaxation times. The resultant distributions of $T_1$ and $T_2$ relaxation times comprise data points of $T_1$ and $T_2$ relaxation curves. These relaxation curves are further processed to extract the dominant $T_1$ and $T_2$ relaxation modes, from which amounts of bound water, free water and hydrocarbons are estimated. The characteristic $T_1$ or $T_2$ times of the surface-wetting phase can also be used to estimate formation pore size distributions and formation permeability, as known in the art.

In a particular application, the $T_1$ and $T_2$ relaxation curves can be used to determine different pore systems residing in carbonate formations and detect the existence of diffusive coupling among different pore systems. In one embodiment, a $T_1$ relaxation curve is obtained and porosity analysis is performed by observing the $T_1$ relaxation curve. The $T_1$ relaxation curve may contain one or more peaks or modes. As known in the art, each peak or mode is associated with a pore system in the formation being analyzed. The size of each pore system can also be estimated based on the relaxation time associated with each peak. For carbonate formations, the $T_1$ relaxation curve is bi-modal, indicating the existence of both a micro and macro pore systems. Additional details of this embodiment are disclosed in application Ser. No. 60/474,747, filed on May 3, 2003, which is incorporated herein by reference.

Applications

Direct Identification of Gas

It is known in the art that methane and more generally gas in the formation has long $T_1$ and, given the gradient of the NMR logging tools, a short $T_2$ value, because of its large diffusivity. This observation can be exploited in the detection of gas in the form of a large $T_1/T_2$ ratio. Methods, such as the differential spectrum method or time domain analysis (TDA), have been designed and used to detect and correct gas by making use of the $T_1$ and $T_2$ contrasts. These differential methods have a drawback, however, because they work on the difference of two signals, which difference can be small particularly in those cases where the hydrogen index (HI) is low, the porosity is low, or invasion is deep. In other words, there are limitations to these approaches, which are important in the proper estimation of total porosity using NMR.

Figure 5:
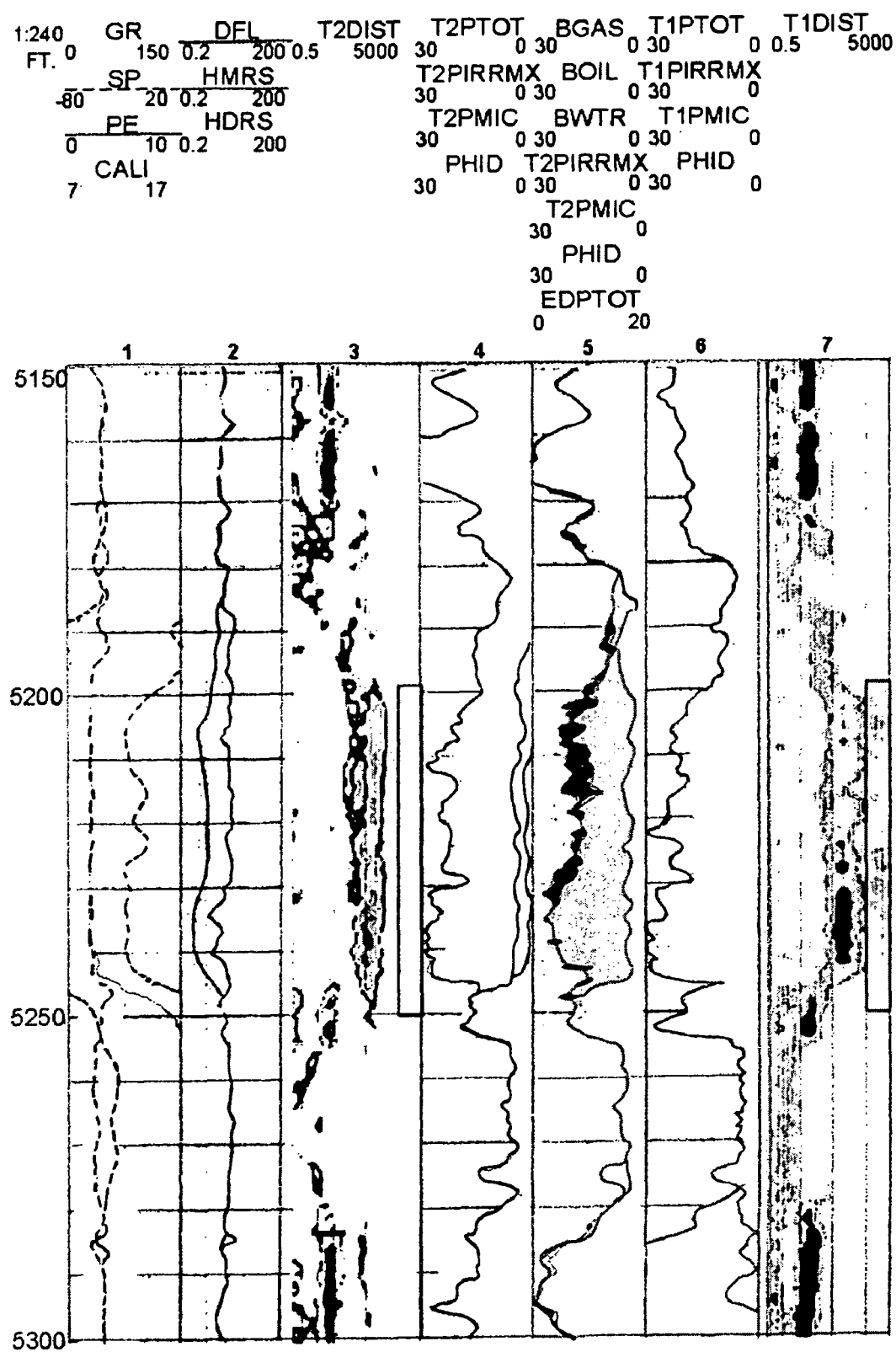
FIGS. 5 and 6 show $T_1$ and $T_2$ logs in a tight gas reservoir to illustrate advantages of $T_1$ logging in accordance with this invention.
Figure 6:
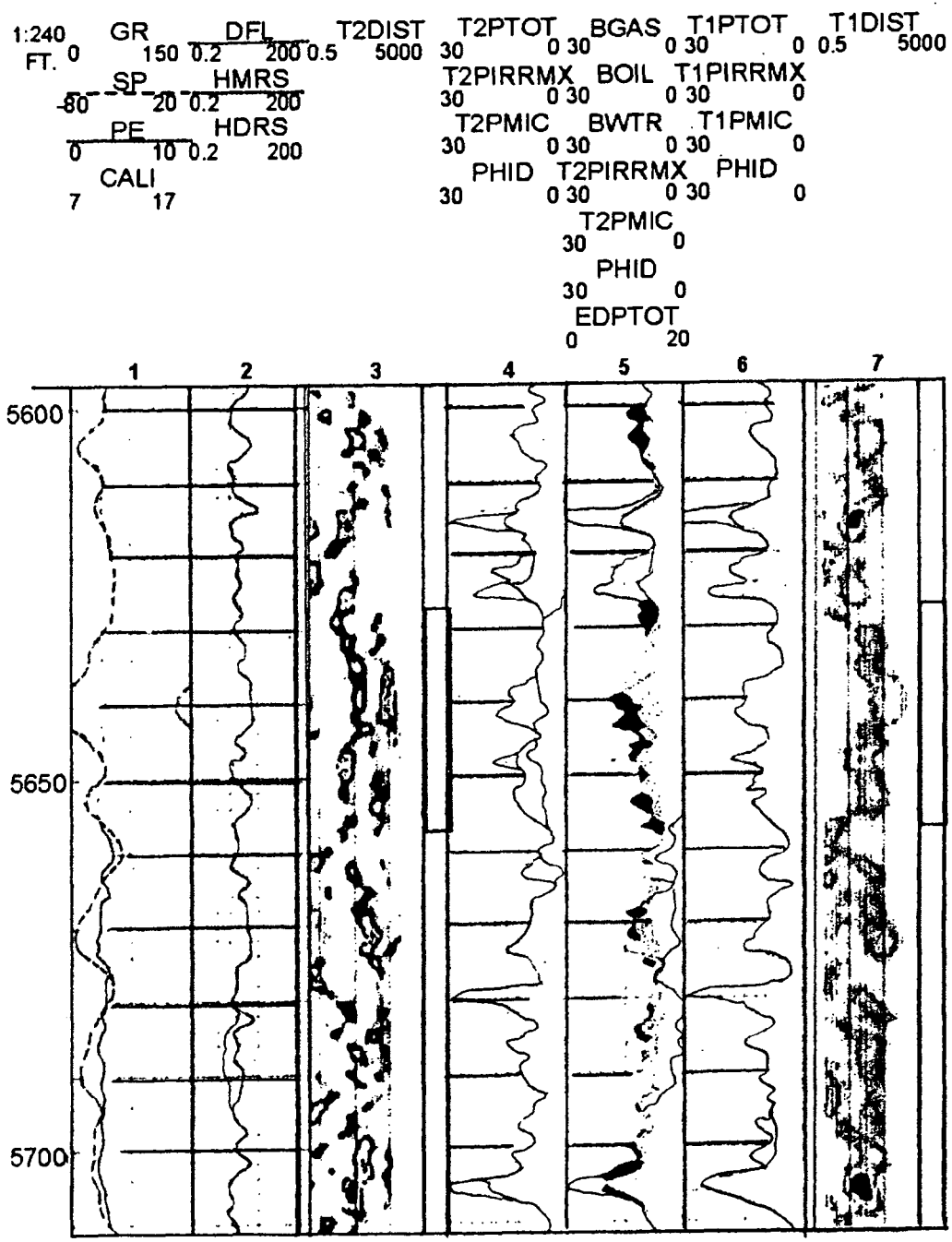

In accordance with the present invention, given knowledge of the rock properties, one can bypass more sophisticated gas identification techniques in certain cases, in particular in applications involving tight gas reservoirs. In a tight gas reservoir, the longest $T_1$ of 100% water saturated rock is no more than a few hundred milliseconds. The $T_1$ of gas, on the other hand, is typically on the order of several seconds. In other words, in a tight gas reservoir, any signal longer than about one second is in all likelihood only due to gas. In accordance with this invention, this observation leads to a novel and simple approach for (i) detecting gas and (ii) correcting the apparent porosity value for gas effects to calculate total porosity. FIGS. 5 and 6 show $T_1$ and $T_2$ logs in a tight gas reservoir, which illustrate this approach. There are seven tracks in each figure, where Track 1 shows Gamma Ray, SP, caliper, PE; Track 2 shows Resistivities; Track 3 shows a VDL of T2 distributions; Track 4 shows Porosities from the T2 Log; Track 5 shows Time Domain Analysis (TDA), generated from T2 logs; Track 6 shows Porosities from $T_1$ log; and Track 7 shows the VDL of the $T_1$ distributions. In each figure the zone of interest is marked by two boxes.

In particular, the zone of interest in FIG. 5 contains sand with residual-gas. Residual condition implies that most of the gas has been produced and the reservoir will produce mostly water and some gas, at least initially. The resistivity logs indicate that water saturations are high, confirming the above conclusion. Nevertheless, there is still some gas in the reservoir and this has been confirmed by gas in the mud logs. Notice that time domain analysis (TDA) in Track 5 shows some gas (dark-shaded area). It is important to notice the corresponding signal in the $T_1$ distribution in Track 7 (even if not very strong because of residual conditions in the case). Since the rocks illustrated in the figure are tight (i.e., have low porosity, low permeability, small pore sizes), such long signal in the $T_1$ distribution is a strong indication of gas. At the same time, one can see that the $T_2$ distribution shown in Track 3 can hardly be interpreted to have gas without the help of TDA.

In FIG. 6, the zone of interest contains no gas, although there are indications in the TDA analysis (Track 5). The gas shown from TDA is not real—it is probably an artifact of dealing with very low porosities in the echo differences. The $T_1$ distribution does not show any gas, especially when compared to FIG. 5. Unlike the section shown in FIG. 5, there were no gas shows in the zone in FIG. 6, confirming the conclusions derived from the $T_1$ log alone.

Based on the above observations, in accordance with the present invention peaks at shorter $T_1$ times are interpreted as being due to water, peaks at longer times (around three to four seconds) are attributed to gas. Thus, in a preferred embodiment, the uncorrected gas filled porosity can simply be obtained directly using the $T_1$ distribution. In particular, selecting a cutoff parameter, which in a preferred embodiment is one second, one can integrate the signal under the $T_1$ distribution to obtain the uncorrected gas filled porosity. Furthermore, knowing the HI parameter of gas (already established a priori, given temperature and pressure), one can make the HI correction in the form at a simple scalar multiplication to obtain a value for total porosity. HI is defined as the number of hydrogen atoms per unit volume relative to that of freshwater at standard temperature and pressure (75.degree. F., 15 psi). Thus the HI value for freshwater is taken as 1.0 and values of HI for other fluids are referenced to this value. HI estimates for various fluids, dependent on temperature and pressure conditions, and how such corrections are applied to provide more accurate porosity estimates are known in the art and need not be considered in detail. Importantly, the above operations do not involve taking the difference of signals, and will thus result in more robust detection since the threshold for detection is much smaller. Also, HI correction for gas in accordance with this invention is very straightforward and can be applied in the field.

Compensating for Insufficient Polarization

Another application of $T_1$ logging in accordance with the present invention is compensation for insufficient polarization. Assuming a single exponential behavior (which can be generalized for the multi-exponential case), the apparent (or measured) porosity is related to the true porosity by $$\phi_a = \phi_t HI(1 - e^{-Tw/T1}) \quad (8)$$

where HI is the hydrogen index; Tw is the wait time; $T_1$ is a longitudinal relaxation time of the fluid; and the subscripts a and t refer to apparent and true, respectively. Given HI=1, measuring the true porosity requires $$1 - e^{-Tw/T1} = 1 \quad (9)$$

which holds if $Tw \approx 5T_{1max}$. Satisfying this requirement for all applications requires explicit knowledge of $T_{1max}$, which is not always available a priori. The current practice is to use a very long wait time, sufficient for all cases, typically in the order of 10 to 12 seconds. Using such a longe wait time in well logging applications forces the use of slow logging speeds, so that reasonable vertical resolution can be maintained.

Although the problem is highlighted for $T_1$ logging here, the same is true for $T_2$ logging. It is known in the art to use different approaches to compensate for insufficient polarization. One such approach is to use a short wait time, no more than about 3 seconds, and apply a polarization correction assuming a known value for the $T_1/T_2$ ratio. The problem is that there are no criteria for determining this value—in order to make the correction properly, one has to know the $T_1$ spectrum. So, in the prior art case, it translates into a fudge factor often determined by observing other porosities, such as crossplot, unnecessarily complicating the analysis and creating the potential for erroneous readings.

In a preferred embodiment of this invention, if the longest wait time in a $T_1$ log is not sufficient for full polarization and there is enough resolution in the $T_1$ axis, one can make a polarization correction given the apparent $T_1$ spectrum and knowledge of acquisition parameters.

In particular, the signal $y_{ij}$ from the jth echo of the ith wait time, given relaxation times $T_{1k}$ and $T_{2k}$ with associated amplitudes $a_k$ is given by:

$$y_{ij} = \sum_{k=1}^{K} a_k (1 - e^{-T_{wi}/T_{1k}}) e^{-jT_e/T_{2k}}, \quad (10)$$

where $T_e$ is the interecho time. Assuming a single echo acquisition from this point on (for purposes of simplification in the notation, without loss of generality), Eq. (10) can be further simplified to drop any dependence on echo number, resulting in $$y_i = \sum_{k=1}^{K} a_k (1 - e^{-T_{wi}/T_{1k}}) e^{-T_e/T_{2k}}. \quad (11)$$

The term in parenthesis is called the polarization factor. The sum of the amplitudes $a_k$ yields the true porosity:

$$\phi_t = \sum_{k=1}^{K} a_k. \quad (12)$$

Considering I wait times and K $T_1$ components; given the data vector d of dimensions (I by 1), and the unknown vector x (I by 1) that contains the amplitudes of the $T_1$ spectrum, the linear system Ax=d is solved using linear least squares techniques to obtain x. The elements of the A matrix (I by K) is given by $$A(i,k) = (1 - e^{-T_{wi}/T_{1k}}) e^{-T_e/T_{2k}}. \quad (13)$$

Note that the relaxation times are fixed a-priori, usually chosen to be equally spaced on a logarithmic grid. Defining $T_{1max}$ as the longest $T_1$ component in the actual $T_1$ spectrum of the fluid, $T_{wmax}$ as the longest wait (recovery) time in the activation (pulse sequence), and the apparent porosity by $$\phi_a = \sum_{k=1}^{K} x_k,$$

one can see that $$\phi_a < \phi_1, \text{ if } T_{wmax} < \alpha T_{1max}, \tag{14}$$

where $\alpha$ is equal to 3 for practical purposes, and is assumed equal to 5 in theory. The condition in Eq. (14) defines the phenomenon known as insufficient polarization, which basically means that the apparent porosity will be less than the true porosity, if the longest wait time is not at least 3 times the longest $T_1$ present in the sample. Thus, the only way to prevent insufficient polarization is to keep $T_{wmax}$ very long, in the order of 12 to 14 seconds. Using such a long wait time is generally impractical, since the long cycle time will lead to very slow logging speeds. In accordance with a preferred embodiment of this invention, one approach to overcoming the insufficient polarization at reasonable logging speeds is to keep $T_{wmax}$ close to $T_{1max}$ (i.e., $T_{wmax} \sim T_{1max}$), and then compensate for the insufficient polarization via signal processing. In a preferred embodiment, compensation is done in a separate processing step applied post-inversion.

Figure 7:
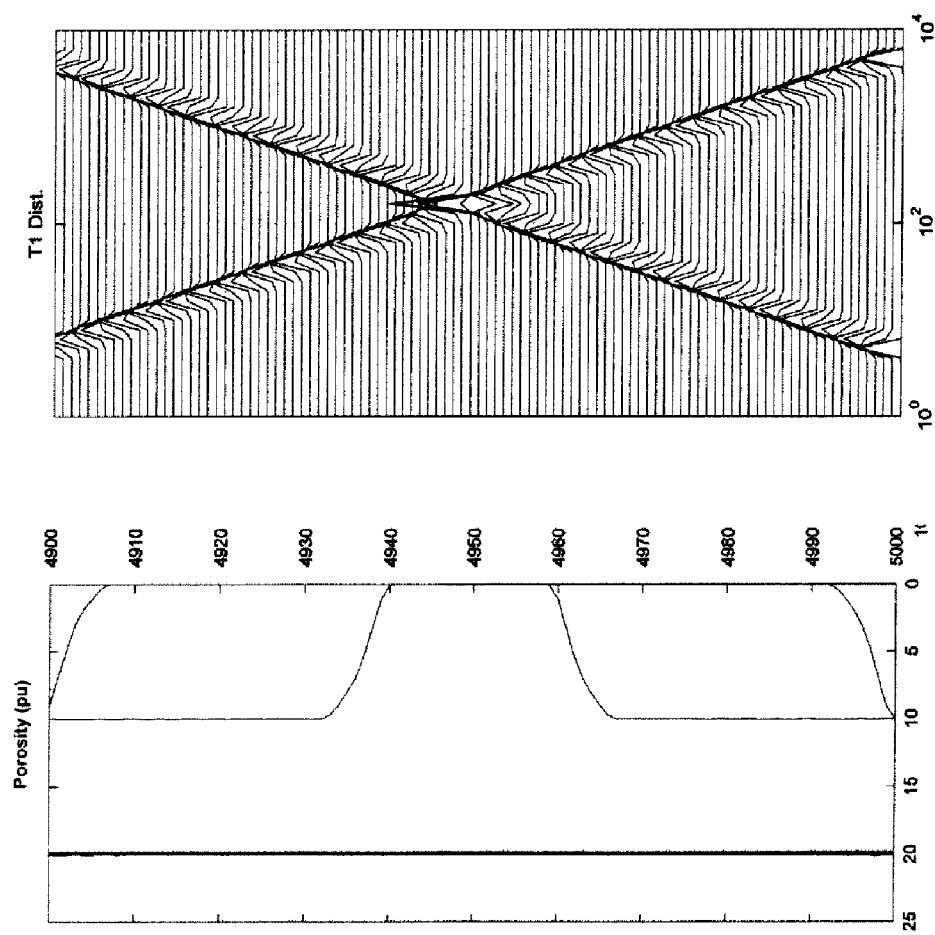
FIG. 7 is a $T_1$ model illustrating insufficient polarization and the post-inversion correction method in accordance with one embodiment of the present invention.

FIG. 7 shows a $T_1$ model illustrating insufficient polarization and the post-inversion correction method in accordance with one aspect of this invention. The porosity log and the $T_1$ spectrum are shown in the left and right tracks, respectively. The straight line in the porosity track shows the input porosity which, as described below, is 20 pu (porosity units). The other two illustrated curves correspond to irreducible and micro porosity. These curves are output automatically by the software, but are not of interest in this modeling study. There are 101 hundred depth points in the model, where the depths range from 4900 ft to 5000 ft. At each point, the input spectrum has two spikes, where each component has an amplitude of 10 pu. While the two components have constant amplitudes, their Tis vary with depth. One component starts at 10 ms at the top of the log, and increases with depth to 5000 ms. The other component starts at 5000 ms at the top of the log, and decreases to 10 ms at the bottom, resulting in a crossing pattern, where a different $T_1$ range is simulated by the model at each depth. Based on these values, $T_{1max}$=5000 ms.

Figure 8:
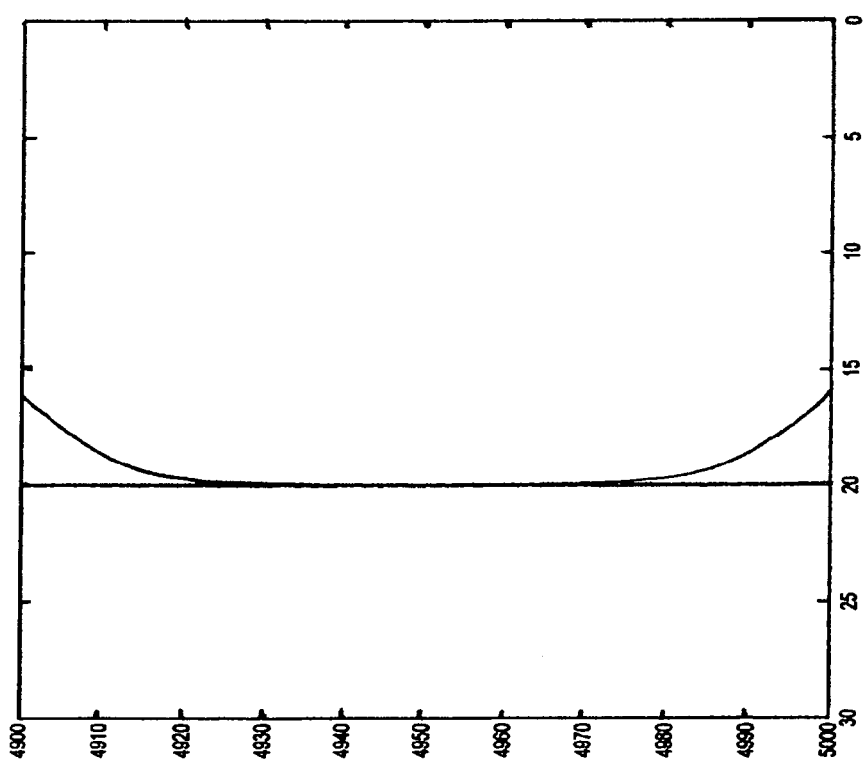
FIG. 8 illustrates the first echo amplitude from the longest wait time as a function of depth.

Based on the model shown in FIG. 7, synthetic logs were generated using 6 wait times ranging from 1 ms to 6300 ms (I=6), and 10 echoes per wait time (J=10) with a Te of 0.5 ms. The acquisition parameters used in the simulations are identical to those used in the real logs presented in the rest of the disclosure. Since each component has a porosity of 10 pu, the apparent porosity from the $T_1$ log, after inversion, should be 20 pu at each depth. However, given the longest wait time of 6300 ms ($T_{wmax}$=6300 ms), the apparent porosity will be less than 20 pu due to insufficient polarization at the top and bottom of the log, since $T_1$ approaches 5000 ms in these end points ($T_{1max}$=5000 ms). This can be best seen from the time domain data, as shown in FIG. 8. In FIG. 8, the first echo amplitude from the longest wait time is shown as a function of depth. Also shown as a straight line is the input total porosity of 20 pu. The departure from the 20 pu line, at the top and bottom of the log, is due to insufficient polarization. The curved line indicates the amplitude of the first echo from the longest wait time. The difference between the two lines is due to insufficient polarization, approaching almost 4 pu at the top and bottom of the log. It will be appreciated that prevention of insufficient polarization via acquisition would require at least a $T_{wmax}$ value of 15000 ms, which is impractical.

Figure 9:
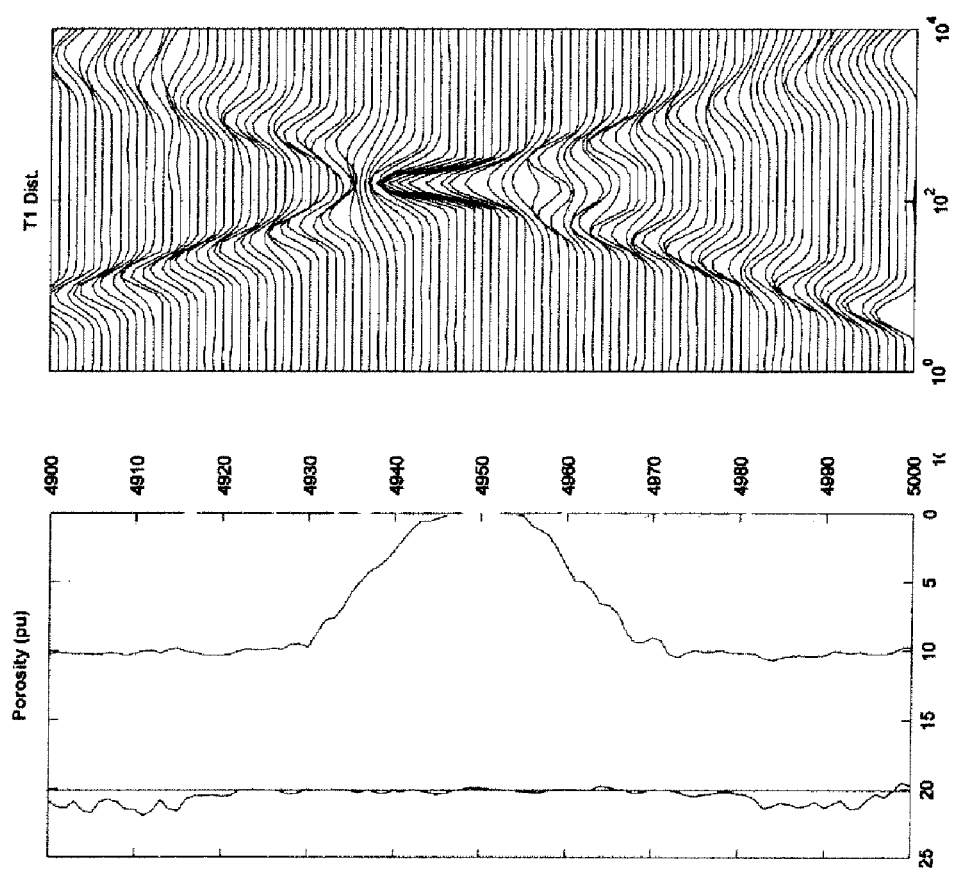
FIG. 9 shows porosity phenomena due to insufficient polarization.

The synthetic logs were generated using a conventional linear least squares algorithm, in particular the MATLAB mathematical software program, which is well known in the art. There are 41 bins in the inversion algorithm (K=41), ranging from 1 ms to 10000 ms. Second-order regularization was applied to prevent oscillations in the distributions. As known, regularization may blur the $T_1$ distributions because while the position of the peaks and the total area under the curve are generally maintained, the regularization process tends to spread the energy into adjacent bins. This may lead to excessive porosity values when the set of time constants $T_{1k}$ used in the inversion contains elements that are longer than $T_{1max}$. This observation is illustrated in FIG. 9. The basis set contains $T_{1k}$ up to 10000 ms, and closer inspection of FIG. 9 shows that there are non-zero amplitudes in bins where $T_{1k}$>5000 ms, even though $T_{1max}$=5000. Inversion automatically compensates for the low polarization factors by boosting the amplitudes associated with these bins.

In accordance with a preferred embodiment, one approach to resolving the issues illustrated in FIG. 9 is to constrain the polarization factors in the A matrix and apply a post-inversion correction. In this approach, the polarization factors in matrix A, only for the longest wait time, are set to 1, as shown below:

$$(1-e^{-T_{wi}/T_{1k}})=1, \text{ for } i=I. \tag{15}$$

Figure 10:
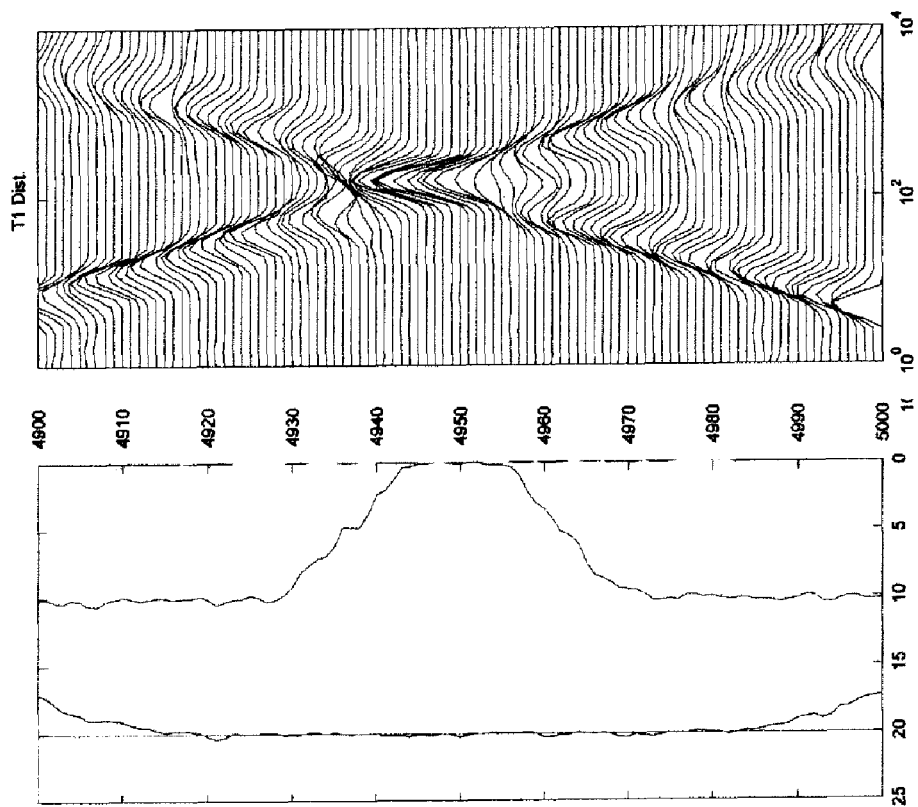
FIG. 10 is shows apparent porosity, where the polarization factors have been corrected for the longest wait times; the results of post-inversion correction in accordance with this invention, applied to the logs shown in FIG. 10 are shown in FIG. 11.

This results in reduced porosities, as shown in FIG. 10, because the amplitudes are not overcompensated. One can see that the apparent porosity is less near the top and the bottom of the log in FIG. 10, similar to the trend observed in FIG. 8. The straight line in the porosity track shows the input porosity (20 pu). The other line is the apparent porosity where the polarization factors are set to 1 for the longest wait time. This results in lower porosity where the $T_1$s are long: at the top and bottom of the log.

The post-inversion correction factors $c_k$, given the amplitudes $x_k$ from inversion, are defined in accordance with one embodiment of this invention by:

$$c_k = \frac{1}{1 - e^{-T_{wi}/T_{1k}}}, \text{ where } i = I. \tag{16}$$

The corrected porosity in a preferred embodiment is then given by:

$$\phi_c = \sum_{k=1}^{K} c_k x_k. \tag{17}$$

Figure 11:
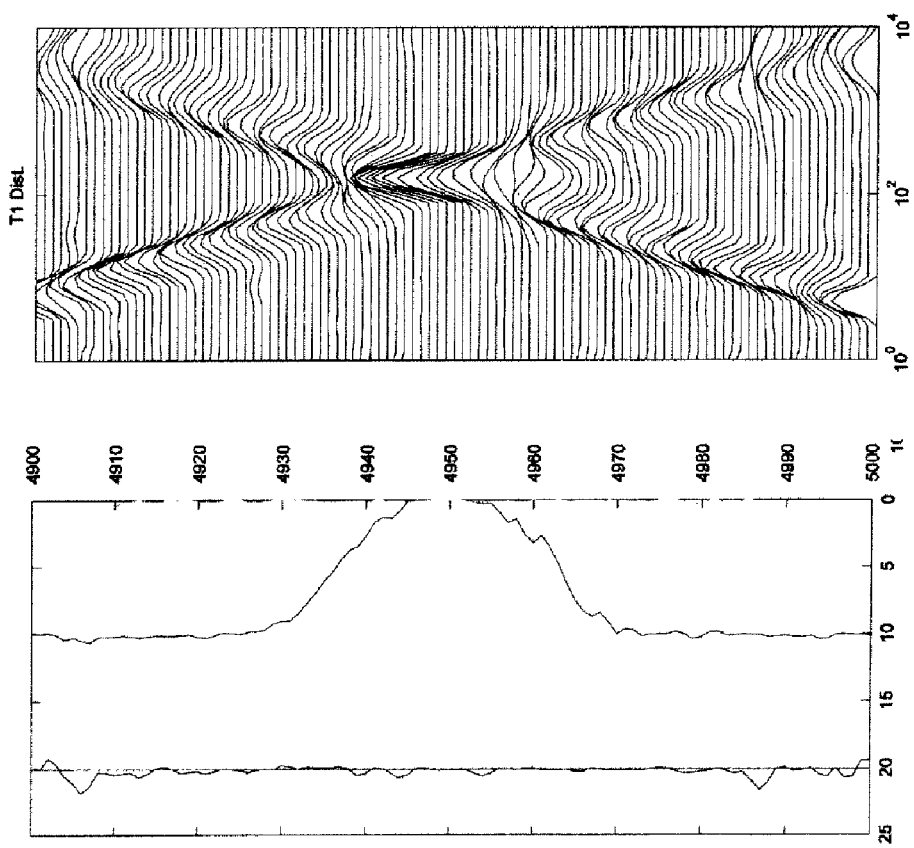

The result of the post-inversion correction applied to the logs shown in FIG. 10 are shown in FIG. 11. As before, the straight line in the porosity track shows the input porosity, which is 20 pu. The superimposed line is the post-inversion corrected apparent porosity, obtained in accordance with one aspect of the present invention. Clearly, except in a few points, the corrected apparent porosity agrees well with the input porosity. The deviations from the trend are not systematic, and are probably due to local variations in the random noise.

A direct benefit of this polarization compensation method applied in accordance with a preferred embodiment of this invention is the potential for increased logging speeds, or increased vertical resolution, since the cycle times are shorter and the data collected are closer spatially. Faster logging applications are considered below.

Faster Logging

NMR logging is relatively slow compared to other openhole logs. Thus, while some other logging tools are run at speeds exceeding 2500 ft/hr, NMR logs are rarely run faster than 1000 ft/hr, which speeds have been realized only recently with the advent of multi-frequency tools such as the MRIL®-Prime, discussed above. One limiting factor on the logging speed is the time it takes for nuclei to polarize. In particular, before an NMR measurement is taken, sufficient time has to be allowed for polarization, because insufficient polarization leads to under-estimation of formation porosity. Accordingly, pre-polarization has become another requirement for fast logging. Modern tools such as the MRIL®-Prime have sufficient pre-polarization that can be utilized in $T_2$ logging. Coupled with a long wait time in the order of 10 to 14 seconds, one can get full polarization in most formations, and this is what makes logging speeds of about 1000 ft/hr feasible. However, there are limitations on how much faster logging can be done without further modifications.

To illustrate the problem, consider the spins subjected to the 90°-pulse at the beginning of the measurement that are left out of the sensitive volume as the tool moves during the course of a typical CPMG pulse sequence. The loss of signal from these spins creates an artifact in the form of additional decay in the NMR signal. The number of the spins that are left out is proportional to the product of v*t, where v is the logging speed and t is measurement time. Obviously at faster logging speeds, the affect is more pronounced. Another problem associated with faster $T_2$ logging is the vertical resolution of the log, which decreases as the logging speed increases. This is especially true for the case of the typical long wait times used in current practice.

Neither of these problems affects $T_1$ logging significantly, as discussed in this application. Spins being flushed out of the sensitive region is not a problem since only a few echoes per wait time are acquired in $T_1$ logging, and the effect due to the loss of spins left out of the sensitive volume during this short time period is insignificant. The resolution is also not a major problem because $T_1$ measurement cycles are generally shorter than their $T_2$ counterparts.

An issue that has to be addressed in fast $T_1$ logging applications is the mixed polarization profile where magnetization originating from pre-polarization ($B_0>0$, $B_1=0$, referred to as pre-pol below) is mixed with magnetization originating from the standard magnets where the antenna is located ($B_0>0$, $B_1>0$, referred to as standard-pol, or just standard). In order to understand this phenomenon, consider the two polarization profiles shown in FIG. 12. In this figure, the magnetization distribution in the sensitive volume at the beginning of the CPMG measurement, for a 24-inch antenna, is shown for two different wait times. The formation modeled has a $T_1$ of 4000 ms, the logging speed is 900 ft/hr, and the wait times are 2 and 12 seconds, from left to right, respectively. The snapshot of magnetization along the length of the antenna is taken immediately after the 90 pulse, just before the first echo of the CPMG.

Figure 12:
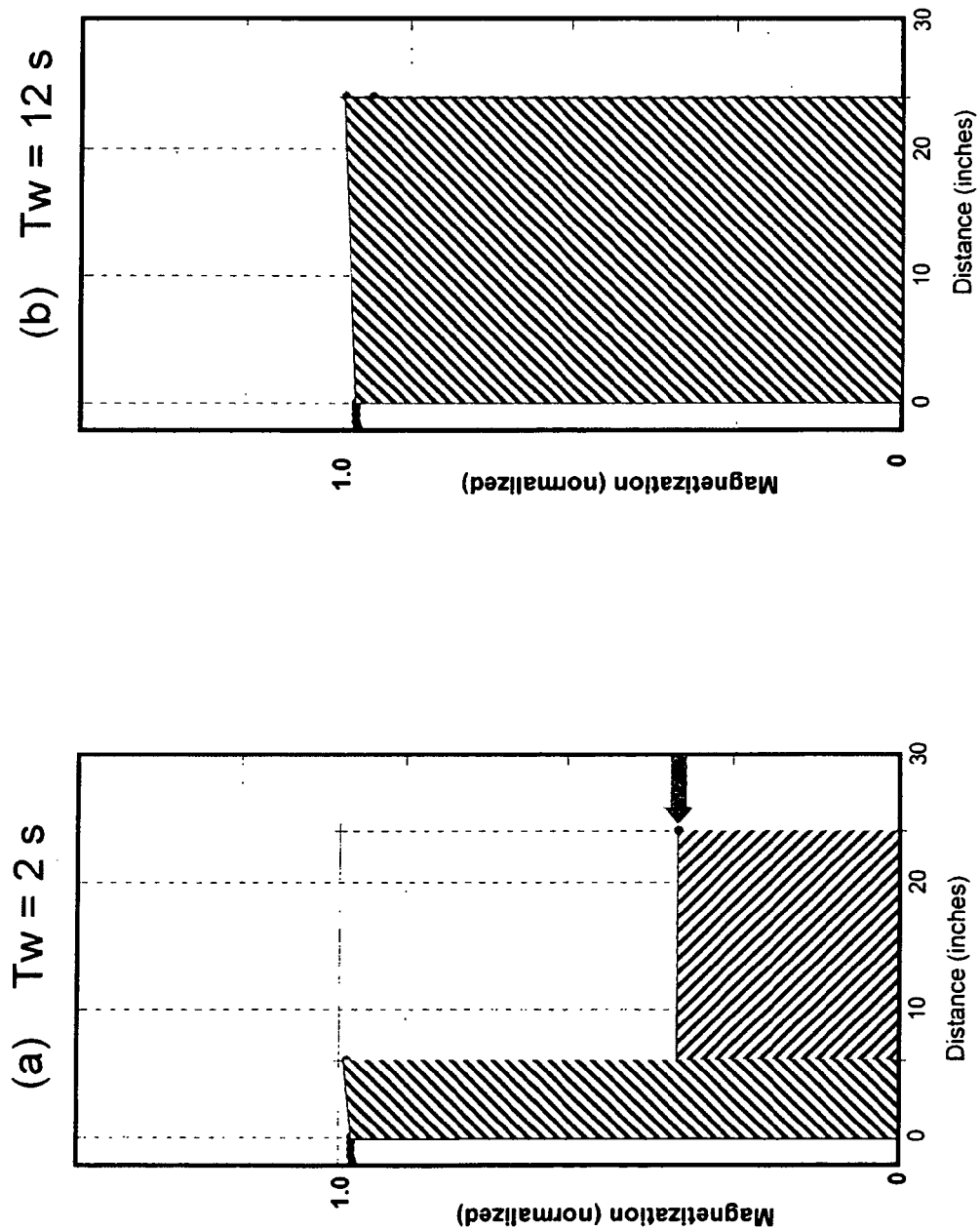
FIG. 12 illustrates polarization profiles used for faster $T_1$ logging in accordance with one aspect of the present invention.

The dark color in FIG. 12 corresponds to the pre-pol component of magnetization, while the gray-color is associated with standard-pol. Note that in the case of the long wait time (FIG. 1(b)), there is no gray-shaded region, all of the magnetization is due to pre-pol and polarization is almost 100%. In the case of the shorter wait time, the magnetization originates from both pre-pol and standard. As can be seen from the difference of the magnetization levels, while magnetization due to pre-pol is almost 100%, the standard-pol portion is about 40%. Note that if the tool logged very slowly, the level of magnetization would be about 40%, there is excess magnetization (or polarization) due to tool motion. This poses a problem, because existing models used in inversion in general do not account for pre-polarization contributions.

To illustrate the problem, consider the following hypothetical case where the porosity of the formation is 100 pu, $T_1$ is 4000 ms, and the wait time is 2000 ms. Based on the profiles shown in FIG. 12, the apparent porosity (assuming that the hydrogen index is 1) in this case would be $$\phi_a = \phi_t * (1 - e^{-T_w/T_1}),$$
$$= 100 * (1 - e^{-0.5}),$$
$$= 39.35.$$

The apparent porosity would be similar if the tool were moving very slowly. However, in the case of fast logging, due to pre-pol, there is more magnetization, and the apparent porosity is almost 55 pu. This is much more than what it is in the stationary case and must be corrected. While the above example illustrates the problem, it also suggests a solution that can be applied in accordance with another aspect of the present invention. In particular, with the addition of a speed related term, the relation between apparent and true porosities can be rewritten as $$\phi_a = \phi_t * p_0 * p_v,$$

where $p_0$ and $p_v$ correspond to polarization factors for the stationary(v=0), and non-zero logging speed cases, respectively. Note that by definition, $$p_0 = 1 - e^{-T_w/T_1}. \quad (18)$$

Hence, with the addition of $p_v$, one can still obtain the true porosity.

Unlike $p_0$, which only depends on the wait time and the $T_1$, the definition of $p_v$ is more complex since it depends not only on the wait time and the $T_1$; but also on the specifics of the pre-polarization and standard magnetic field distributions, and the logging speed. The values for $p_v$ can be computed in a preferred embodiment given knowledge of tool design parameters. Thus, in the hypothetical example used above, $p_v=1.3924$, for v=900 ft/hr and $T_w=2000$ ms, $T_1=4000$ ms.

If the polarization due to pre-pol is explicitly accounted for in the inversion, the complications due to tool motion vanish. Going back to the linear system defined for the $T_1$ problem (See, Eq. 13):

$$Ax=d,$$

$$A(i,k)=(1-e^{-T_{wi}/T_{1k}})e^{-T_e/T_{2k}},$$

one can redefine the A matrix for the speed effects as below $$A(i,k,v)=p_0(i,k)p_v(i,k,v)e^{-T_e/T_{2k}}, \quad (19)$$

where $p_0$ is defined as in Eq. (18), and the factors dependent on $p_v$ can be determined for a particular tool design a-priori using modeling, or through measurements for a particular tool design and acquisition parameters. Note that the $p_v$ terms change depending on the logging speed, which changes can be accounted for using the illustration in FIG. 12. Solution of the linear system with the modified A matrix in Eq. 19 yields the correct porosity.

The advantage of explicitly accounting for pre-polarization magnetization is that one does not have to seek 100% polarization, as shown in FIG. 12(b). Since the sources of polarization are accounted for explicitly, one can resort to shorter wait times (for example a maximum of 3 seconds instead of 12), and thus increase logging speed significantly. Use of such wait times shorten the cycle time for the $T_1$ measurement, which helps retain good vertical resolution at high logging speeds.

Estimation of Diffusivity and Gas-to-Oil Ratios

Given two $T_2$ logs, acquired with different Te's to (inter-echo times), one can estimate of diffusivity of light hydrocarbons using the relationship.

$$\frac{1}{T_{2,hc}} = \frac{1}{T_{1,hc}} + \frac{D_{0,hc} \cdot (G.\gamma.TE)^2}{12}$$

as explained in the examples below. In particular, a $T_1$ log can be considered as a $T_2$ log acquired with an infinitely short $T_e$ (no diffusion effects). Hence, the combination of a $T_1$ log and a $T_2$ log can be used in accordance with the present invention to estimate directly the diffusivity of the hydrocarbons phase. Furthermore, in another aspect of the invention once the diffusivity is estimated, one can estimate the gas to oil ratio (GOR), combining the $T_1$ value with the $D_0$ value. An illustration is provided in the following section of the disclosure on Practical Examples.

PRACTICAL EXAMPLES $T_1$ versus $T_2$ Logging

The $T_1$ inversion used in commercial applications, wireline or LWD, uses generally all the data available, which is typically 10 echoes per CPMG trainlet. Single echo inversion is either limited to qualitative processes, such as the Reconnaissance Mode (described in paper SPE 62981 presented at the 2000 SPE conference), or to those very high SNR applications, such as the MRILab™ tool where SNR is typically in the order of 200 or better. All the results presented herein, as well as those presented in previous publications (paper DDD, presented at the 43rd Annual Logging Symposium, Osio, Japan; paper SPE 77395 presented at the 2002 SPE Annual Technical Conference and Exhibition) use 10 echoes per CPMG. The inter-echo time in all these cases is either 0.51 ms or 0.6 ms. All papers identified in this paragraph are incorporated herein by reference for background.

Figure 13:
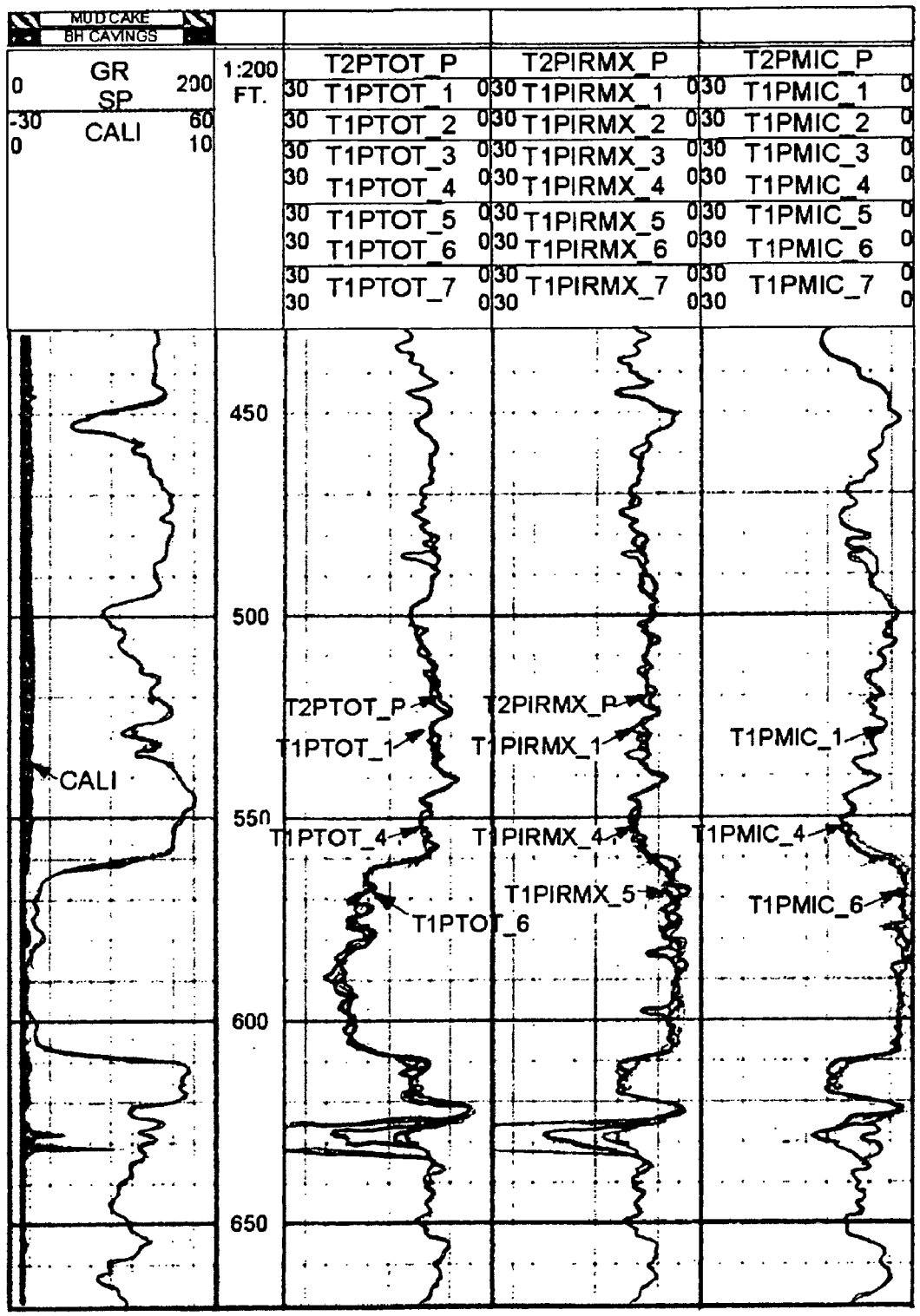
FIG. 13 shows porosity logs verifying the quality of petrophysical determinations from $T_1$ measurements by comparison to corresponding $T_2$ logs in simulated-drilling mode.

The porosity logs displayed in FIG. 13 verify the quality of petrophysical answers from $T_1$ measurements and demonstrate their robustness and repeatability. Data from eight different runs, in the same well, are presented in this figure including: a wireline MRIL®Prime $T_2$ log; an MRIL-WD™ $T_1$ log acquired while drilling the well; and six MRIL-WD™ $T_1$ logs acquired in simulated-drilling mode, where the tool was rotated while going up or down in the well.

Track 1 in FIG. 13 shows GR, SP and Caliper logs. Track 2 shows the total porosity from all runs (xxPTOTxx), whereas Tracks 3 and 4 show the irreducible and micro porosity curves, respectively (xxT2PIRMXxx, xxPMICxx). The prefix $T_1$ or $T_2$ is used to distinguish $T_1$-based curves from $T_2$-based curves. The main reservoir is between 550 to 610 feet, and is logged in each pass. Some of the passes do not cover the shallower portions of the well, and some logs terminate above the washout at 620 feet. The standard deviation of the total porosity from the $T_1$ logs is 0.94 pu, and the standard deviation of the irreducible fluid porosity from the same is 1.06 pu. The excellent repeatability among the $T_1$ logs, as well as the close agreement with the benchmark MRIL®-Prime $T_2$ log should leave no doubt as to the validity and quality of the $T_1$ measurement results. It should be noted also that the comparisons are made using the more challenging LWD logs, not wireline logs.

Case Study

As part of a pilot study, a series of wireline $T_1$ logs were run to assess the operational and petrophysical feasibility of this novel application. This study was assisted by access to a major core study that includes NMR $T_1$ data.

Figure 14:
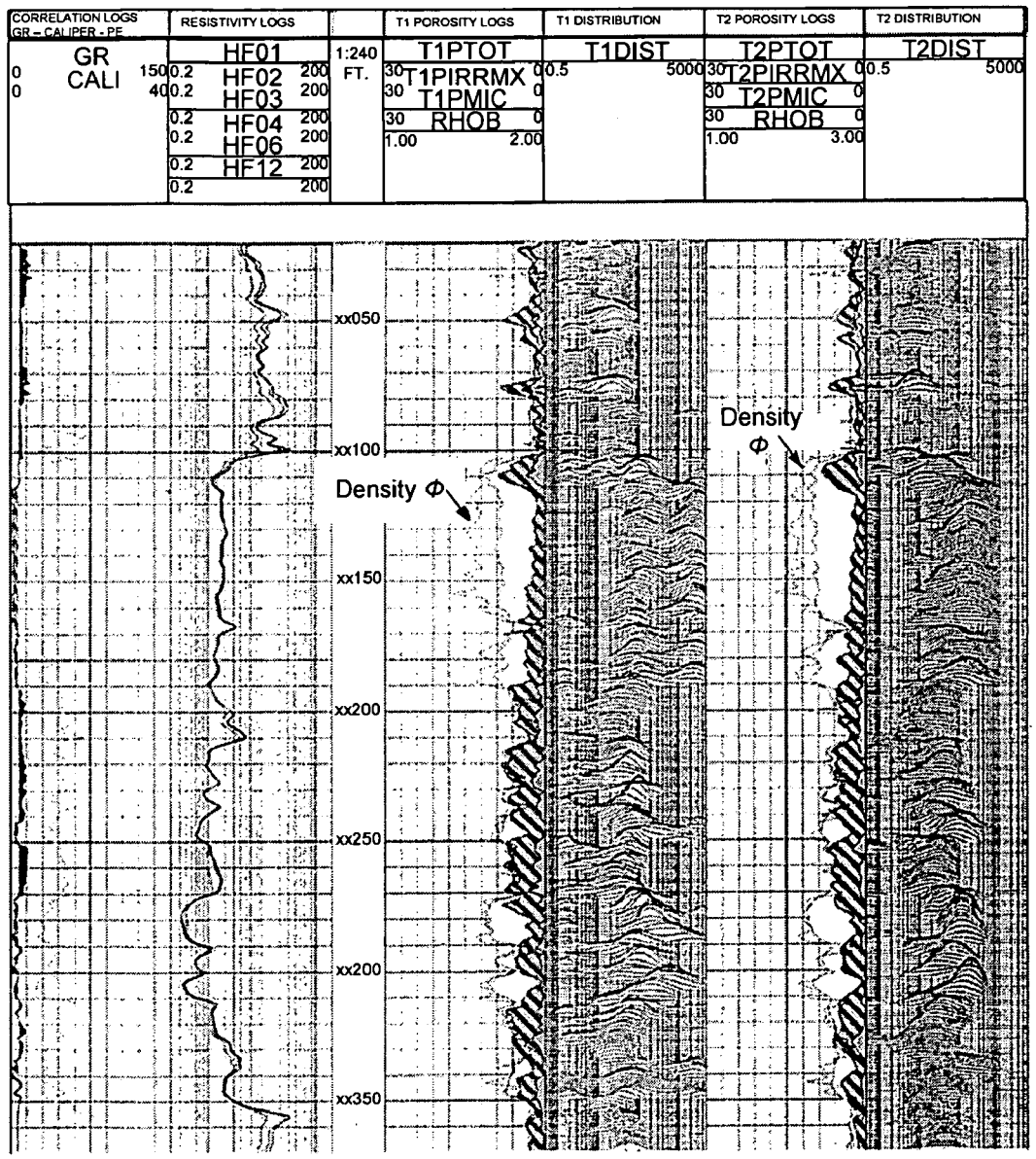
FIG. 14 illustrates a series of wireline $T_1$ logs used to assess the operational and petrophysical feasibility of the novel approaches in accordance with the invention.

The logs presented here in FIG. 14 are from the very first well in the program. This well was drilled with an 8½" bit using salt-saturated mud, which resulted in a fairly smooth well bore with some washed-out zones in the non reservoir carbonate section, and only marginal enlargement and mud-cake buildup in the deeper sandstone reservoirs.

A full suite of openhole logs was acquired in tool-push mode including caliper, GR, SP, resistivity, density, neutron, acoustic, formation tester (pressures only), and borehole images. A standard MRIL®-Prime™ tool was run to acquire a dual wait time $T_2$ log, followed by a $T_1$ log over the same interval. Bore hole enlargement is indicated with dark shading, mud-cake build-up by the gray shading. The second track shows six array-resistivity curves at different investigation depths. Breakdown of the MRIL®$T_1$ porosity in micro (dark gray), irreducible (dark, striped gray) and moveable (light gray) porosity is presented in the third track. Density porosity is shown as reference. The gray-shaded $T_1$ spectra are on a log scale from 0.5 ms to 5 s. Track 5 presents the breakdown of MRIL®$T_2$ porosity, using the same shadings as before with the $T_2$ spectra (gray shading) in the adjacent track.

NMR core data from an offset well were available from an earlier, large-scale laboratory NMR core study. The main objective of this core study was to improve NMR log interpretation by establishing field specific parameters for e.g. spectral- and cut-off BVI, permeability, etc. $T_1$ measurements were already included in the program, in anticipation of future $T_1$ based applications. The benefits of this core study were immediately realized during the interpretation of the well, particularly in the determination of hydrocarbon types.

The basic log panel in FIG. 14 shows the openhole logs, where the reservoir sands start at a depth of about xx100 ft. The main zone of interest starts with 90 feet of clean and homogeneous sand, intersected 65 ft from the top by a -most likely sealing- tight streak. There are several poorer quality wet sands below the main pay zone, followed by another small pay zone located between xx335 to xx350 ft. The pay zones can easily be identified from the difference (under call) between the apparent density and NMR (either $T_1$ or $T_2$) porosity logs. Note that the same logs agree very well in the wet zones. Also, note the resistivity logs show no signs of significant invasion.

The $T_1$ log exhibits bi-modal distributions in the pay zones, whereas the $T_2$ logs are generally uni-modal. Also, the comparison of uncorrected $T_1$ and $T_2$ porosities in the pay zone reveals that the porosity from the $T_2$ log is higher than $T_1$ porosity. This can be explained by the fact that the $T_2$ log has a longer wait time. The longest recovery time in the $T_1$ log is 6.3 seconds, while the wait time in the $T_2$ log is 12.0 seconds. Obviously, more polarization occurs in the case of the longer wait time when the reservoir fluid has a long TV. Using the rule-of thumb of three times the $T_1$ for full polarization, one can estimate that the $T_1$ of the hydrocarbon is at least 2.1 seconds.

While a $T_1$ value longer than 2.1 seconds would be consistent with the expected hydrocarbon type of dry gas, apparent $T_1$ porosity (uncorrected for hydrogen index or incomplete polarization), and the $T_1$ distributions indicate a different fluid, as discussed next.

The $T_1$ distributions show a very clear bi-modal distribution in the pay zones, where the long $T_1$ peak is centered about 3 seconds. Since such a peak is not observed in the wet zones, this peak can be easily attributed to the presence of gas. However, using a $T_1$ cutoff of 1 second, and applying gas corrections to the log (i.e., accounting for partial polarization and factoring in the Hydrogen Index of 0.48 for natural gas under the pressure and temperature conditions encountered in this well), results in a porosity that is significantly higher than what has been observed field wise. Simply put, the signal associated with the long $T_1$s in the pay zone can not be attributed to dry gas only. There are two possibilities: (1) some of the signal is due to invasion water, (2) the hydrocarbon is not just methane, but contains heavier components (which effectively increases the HI, reduces the HI-correction and hence the apparent porosity).

Figure 15:
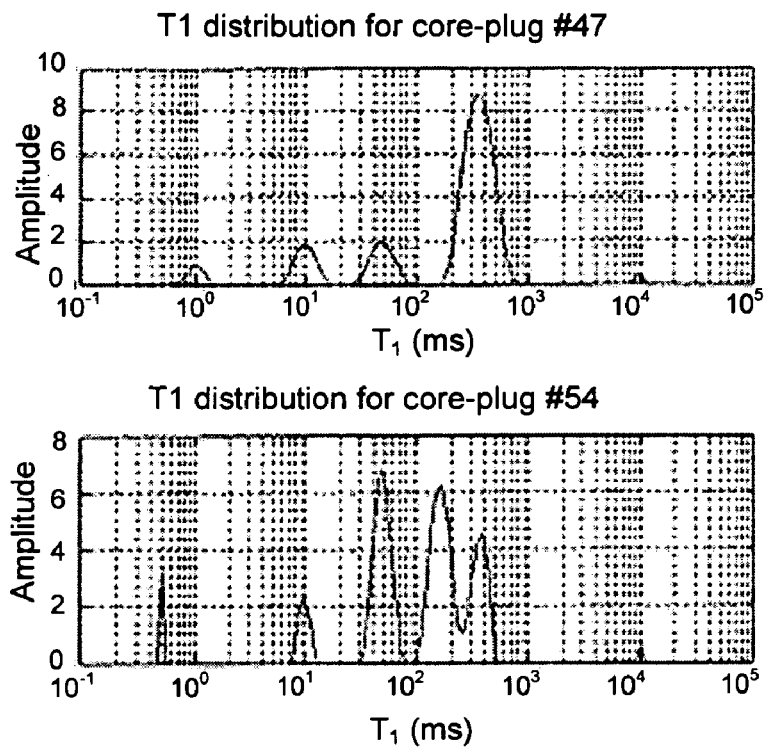
FIG. 15 shows NMR spectra from two core plugs

NMR spectra from two core plugs that were included in the before mentioned core study, are shown in FIG. 15. These plugs were taken from the core from an offset well. They were first cleaned, then saturated with water (Sw=100%) and subjected to a series of conventional petrophysical measurements, as well as NMR $T_1$ and $T_2$. There is clearly no support for long $T_1$s in the fully saturated core data: the slowest $T_1$ components relax at a rate much faster than 1 second. This rules out possibility #1 to reduce the apparent porosity, only leaving the possibility that we're not dealing with just dry gas, but also with heavier components.

Ruling out the presence of dry gas helps explain the trends observed in the $T_2$ log. Analysis of dual wait time ($T_2$) data shows differential amplitudes in the pay sands centered on $T_2$ values of approximately 200-300 ms, instead of the 35 ms that would be expected in the case of gas. This confirms the interpretation that the reservoir fluid is not gas, but a very light hydrocarbon instead. The $T_1$ and $T_2$ of the hydrocarbon phase are 3.5 and 0.3 s, respectively. The large $T_1/T_2$ ratio indicates a large $D_0$ value, (see the discussion on estimation of $D_0$ and GOR). Due to the large diffusivity of the hydrocarbon phase, the water and hydrocarbon signals overlap in the $T_2$ domain, but are well separated in $T_1$ domain. Lack of diffusion effects in the $T_1$ log actually result in easier identification of the pay zones for this reservoir.

Figure 16:
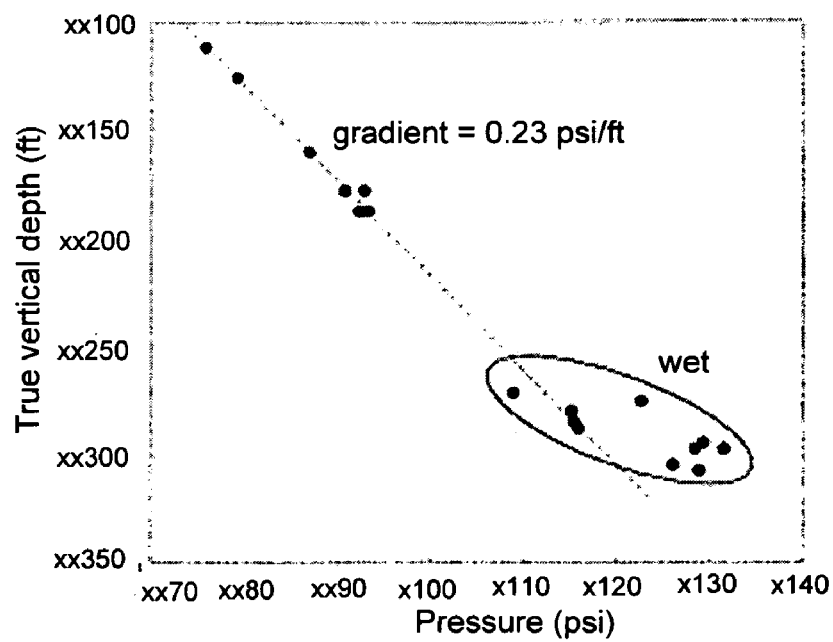
FIG. 16 shows the pressure data in a well, confirming the NMR-based interpretation in accordance with the present invention.

FIG. 16 displays the pressure data in the well, confirming the NMR-based interpretation: the pressure gradient in the pay sand (Group 1; dots in the top left corner) is established at 0.23 psi/ft, which corresponds to a density of 0.53 g/cm3, indicative of a light hydrocarbon indeed. When entering the wet zones, there is a distinct change in the gradient.

The interval xx190-xx270 ft is of poor to non reservoir quality with some inter-bedded cleaner layers. The sand body starting at xx270 ft is again of reservoir quality; the NMR logs, however, match the density-derived porosity values much closer, indicating a different (mixture of) reservoir fluid. The much weaker differential signal appears again at $T_2 \approx 200$ ms, suggesting that the reservoir is only partially hydrocarbon filled at these depths. Based on the similarities in $T_1$ and $T_2$ characteristics, the hydrocarbon is thought to be the same light oil as encountered higher up in the well. Log analysis, using conventional data in combination with NMR porosity, confirms this interpretation and shows an abundance of free water with some pockets of gas.

The MRIL® $T_1$ and $T_2$ data corroborate this interpretation. Sands of reservoir quality exhibit $T_2$ peaks well in excess of 50 ms; most center on 200 ms. Wherever these $T_2$ peaks occur in combination with the distinct $T_1$ peaks of some 2 s, we are dealing with light (high GOR) oil, whereas the other zones are wet.

Estimation of GOR

Under the assumptions that the reservoir is water-wet and that for the hydrocarbon, $T_{1,bulk} \approx T_{2,bulk}$, equations 1 and 2 can be combined and re-written as:

$$\frac{1}{T_{2,hc}} = \frac{1}{T_{1,hc}} + \frac{D_{0,hc} \cdot (G.\gamma.TE)^2}{12} \quad (20)$$

Figure 17:
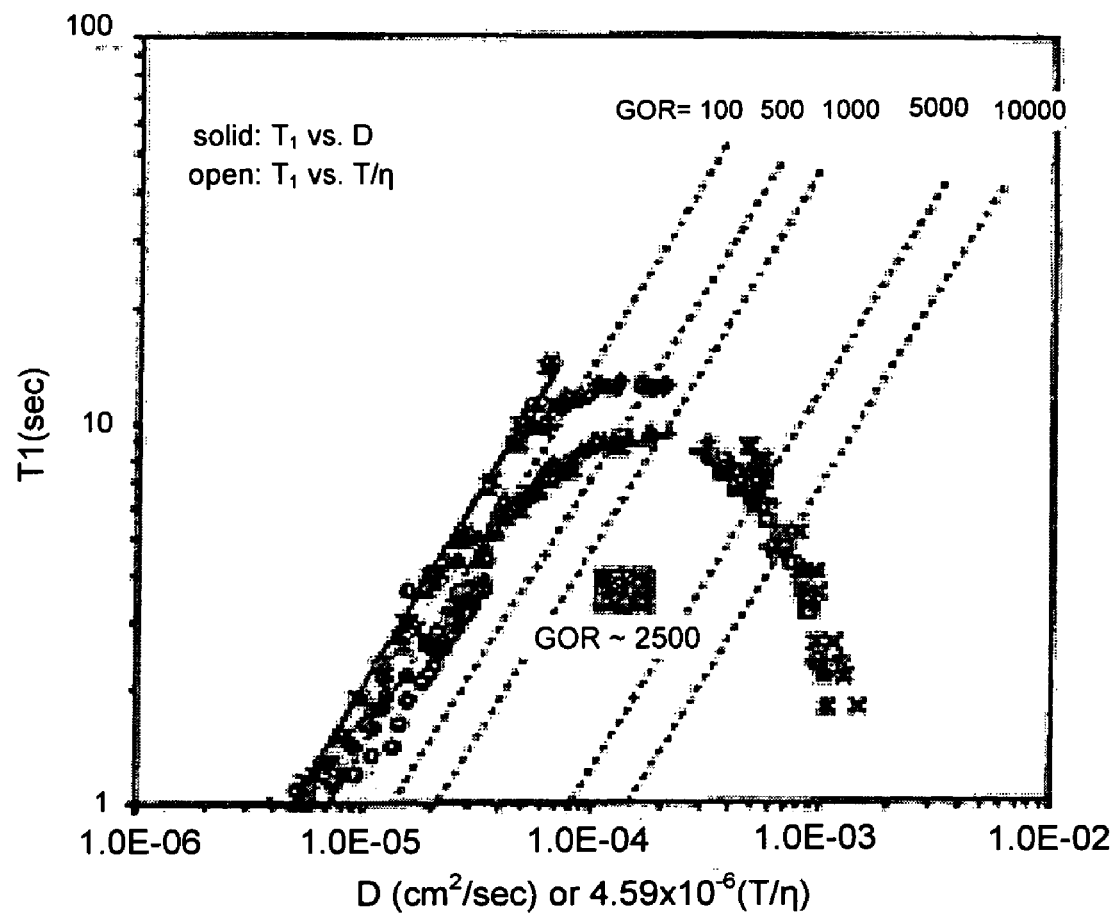
FIG. 17 shows estimation of gas to oil ratio (GOR) in accordance with the present invention.

Stacking the echo-trains (trainlets) over the entire pay-zone, followed by inversion, yields $T_{1,hc} \approx 3.5$ s and T2,hc≈300 ms. These values, combined with the tool parameters in eq. (8) indicate that the viscosity of the light oil in this reservoir is on the order of 13×10-5 cm2 /s. Using the correlations by Lo et al. (paper SPE 63217 presented at the 2000 SPE Annual Technical Conference and Exhibition, Dallas, Tex.) of $T_1$ relaxation times with diffusivity $D_0$ and Gas-to-Oil Ratios (GOR), estimates the GOR in this reservoir at≈2500. This solution is indicated by the solid dot in FIG. 17. Analyzing the sensitivity of this result with respect to the parameters derived from the logs (mainly $T_{1,hc}$ and $T_{2,hc}$) shows that GOR fits in the range 1000-4000, indicated by the dark-shaded area in FIG. 17. For details on computing the GOR estimates the interested reader is directed to Lo et al., paper SPE 63217 presented at the 2000 SPE Annual Technical Conference and Exhibition, Dallas, Tex., 1-4 Oct., 2000.

Based on the above, it is apparent that $T_1$ information alone already adds significant value petrophysically and helps delineating the reservoir fluids and establishing fluid contacts. It was further demonstrated that the measurements have excellent robustness and repeatability, similar to wireline $T_2$ logs run under comparable conditions. Given field knowledge, $T_1$ logging can be used very easily to recognize hydrocarbon bearing zones, and simple cutoff techniques can be used to correct for hydrocarbon effects, since the hydrocarbon phase is easily and directly identified. It was demonstrated that when combined with $T_2$ log(s), $T_1$ logs can be utilized to determine diffusivity, GOR and viscosity at reservoir conditions of (light) hydrocarbons. Importantly, $T_1$ saturation recovery logs used in accordance with the present invention are more compact than CPMG $T_2$ logs and can run faster, since their total measurement time is generally shorter compared to $T_2$ logging. The combinations discussed above are believed to be a significant contribution to the art of NMR logging with wide ranging applications involving virtually all NMR tools, and a broad range of practical applications, including both wireline and LWD/MWD.

While the invention has been described with reference to the preferred embodiments, it will be appreciated by those of ordinary skill in the art that modifications can be made to the structure and form of the invention without departing from its spirit and scope which is defined in the following claims.

Nomenclature $D_0$=coefficient for molecular self diffusion, 10-5 cm2/s
G=magnetic field gradient, gauss/cm
GOR=Gas Oil Ratio, v/v
GR=Gamma Ray (log)
HI=Hydrogen Index
NE=number of echoes in CPMG sequence
PE=Photo Electric (log)
S=surface area of pore space, cm2
SP=Spontaneous Potential (log)

Te=echo spacing, ms
$T_1$=longitudinal relaxation time (distribution), ms
$T_2$=transverse relaxation time (distribution), ms
Tw=recovery time for magnetization to build-up
V=volume of pore space, cm3
φ=porosity, p.u.
γ=gyro magnetic ratio, 2π*4258 Hz/gauss for protons
ρ=surface relaxivity, cm/ms References of Potential Interest
1. Brown, R. J. S., and Gamson, B. W., 1959: "Nuclear Magnetism Logging," Society of Petroleum Engineers, presented at the 34th Annual Fall Meeting, Dallas, Tex., October 4-7.
2. Timur, A., 1968: "Effective Porosity and Permeability of Sandstones Investigated Through Nuclear Magnetic Resonance Principles," Paper K, SPWLA, presented at the 9th Annual Logging Symposium, New Orleans, La.
3. Kenyon W. E., Howard, J. J., Sezginer, A., Straley, C., and Matteson, A., 1989: "Pore-size Distribution and NMR in Microporous Cherty Sandstones," Paper LL, SPWLA, presented at the 30th Annual Logging Symposium, Denver, Colo.
4. Prammer, M. G., Akkurt, R., Cherry, R., and Menger, S., 2002: "A New Direction in Wireline and LWD NMR," paper DDD, presented at the 43rd Annual Logging Symposium, Osio, Japan.
5. Prammer, M. G., Drack, E., Goodman, G., Masak, P., Menger, S., Morys, M., Zannoni, S., Suddarth, B., and Dudley, J., 2000: "The Magnetic Resonance While Drilling Tool: Theory and Operation" paper SPE 62981 presented at the 2000 SPE Annual Technical Conference and Exhibition, Dallas, Tex., 1-4 October.
6. Prammer, M. G., Bouton, J., and Masak, P., 2001: "The Downhole Fluid Analyzer," paper N, SPWLA, presented at the 42nd Annual Logging Symposium, Houston, Tex.
7. Morley, J., Heidler, R., Horkowitz, J., Luong, B., Woodburn, C., Poitzsch, M., Borbas, T., and Wendt, B., 2002: "Field Testing of a New Nuclear Magnetic Resonance Logging While Drilling Tool", paper SPE 77477 presented at the 2002 SPE Annual Technical Conference and Exhibition, San Antonio, Tex., 29 September-2 October.
8. Appel, M., Radcliffe, N. J., Aadireddy, P., Bonnie, R. J. M., and Akkurt, R, 2002: "Nuclear Magnetic Resonance While Drilling in the U.K. Southern North Sea", paper SPE 77395 presented at the 2002 SPE Annual Technical Conference and Exhibition, San Antonio, Tex., 29 Sep.-2 Oct., 2002.
9. Lo, S.-W., Hirasaki, G. J., House, W. V. and Kobayashi, R., 2000: "Correlations of NMR Relaxation Times with Viscosity, Diffusivity and Gas/Oil Ratio of Methane/Hydrocarbon Mixtures" paper SPE 63217 presented at the 2000 SPE Annual Technical Conference and Exhibition, Dallas, Tex., 1-4 October.

What is claimed is:

1. A method for analyzing geologic formations, comprising the steps of:
    obtaining a first set of $T_1$ NMR measurements of the geologic formation;
    obtaining at least one second set of $T_2$ NMR measurements of the geologic formation; and
    processing said first and at least one second sets of NMR measurements to derive an estimate of one or more of: diffusivity, gas to oil ratio (GOR) and viscosity at reservoir conditions, wherein the estimate is obtained from the $T_1$ NMR measurements and the $T_2$ NMR measurements as a function of $T_{2,hc}$, $T_{1,hc}$, G, TE, where G is the gradient of the magnetic field and the $T_1$ NMR measurements are used to approximate $T_2$ NMR measurements with an infinitely short $T_E$.

2. The method of claim 1, wherein an estimate of diffusivity is obtained for diffusivity of low viscosity light hydrocarbons.

3. The method of claim 1, wherein an estimate of diffusivity $D_0$ is obtained directly from the $T_1$ NMR measurements and the $T_2$ NMR measurements using:

$$\frac{1}{T_{2,hc}} = \frac{1}{T_{1,hc}} + \frac{D_{0,hc} \cdot (G.\gamma.TE)^2}{12}$$

where G is the gradient of the magnetic field, γ is the gyromagnetic ratio and the $T_1$ NMR measurements are considered as being acquired with an infinitely short $T_E$.

4. The method of claim 1, wherein an estimate of GOR is obtained by combining a $D_0$ estimate and $T_1$ values.

5. The method of claim 1, further comprising a step of pre-polarizing the geologic formation.

6. The method of claim 1, further comprising a step of compensating for insufficient polarization within the geologic formation.

7. The method of claim 1, further comprising a step of delineating reservoir fluids based on the one or more derived estimate.

8. The method of claim 1, further comprising a step of identifying hydrocarbon bearing zones based on the one or more derived estimate.

9. The method of claim 1, further comprising the step of processing the $T_1$ NMR measurements and an estimate of diffusivity.

10. The method of claim 1, further comprising the step of plotting the $T_1$ NMR measurements and an estimate of diffusivity.

11. A system for analyzing geologic formations, comprising:
    means for obtaining a first set of $T_1$ NMR measurements of the geologic formation;
    means for obtaining at least one second set of $T_2$ NMR measurements of the geologic formation; and
    means for processing said first and at least one second sets of NMR measurements to derive an estimate of one or more of: diffusivity, gas to oil ratio (GOR) and viscosity at reservoir conditions, wherein the means for processing said first and at least one second sets of NMR measurements is configured to derive an estimate from the $T_1$ NMR measurements and the $T_2$ NMR measurements as a function of $T_{2,hc}$, $T_{1,hc}$, G, TE, where G is the gradient of the magnetic field and the $T_1$ NMR measurements are used to approximate $T_2$ NMR measurements with an infinitely short $T_E$.

12. The system of claim 11, wherein the means for processing said first and at least one second sets of NMR measurements is configured to derive an estimate of diffusivity for diffusivity of low viscosity light hydrocarbons.

13. The system of claim 11, wherein the means for processing said first and at least one second sets of NMR measurements is configured to derive an estimate of diffusivity $D_0$ directly from the $T_1$ NMR measurements and the $T_2$ NMR measurements using:

$$\frac{1}{T_{2,hc}} = \frac{1}{T_{1,hc}} + \frac{D_{0,hc} \cdot (G.\gamma.TE)^2}{12}$$

where G is the gradient of the magnetic field, $\gamma$ is the gyromagnetic ratio and the $T_1$ NMR measurements are considered as being acquired with an infinitely short $T_E$.

14. The system of claim 11, wherein the means for processing said first and at least one second sets of NMR measurements is configured to obtain an estimate of GOR based on a $D_0$ estimate and $T_1$ values.

15. The system of claim 11, further comprising means for pre-polarizing the geologic formation.

16. The system of claim 11, wherein the means for processing said first and at least one second sets of NMR measurements is configured to compensate for insufficient polarization within the geologic formation.

17. The method of claim 9, wherein the step of processing the $T_1$ NMR measurements and the estimate of diffusivity is used to derive formation properties.

18. The method of claim 9, wherein the step of processing the $T_1$ NMR measurements and the estimate of diffusivity is used to derive fluid properties.

19. The system of claim 11, further comprising means for processing the $T_1$ NMR measurements and an estimate of diffusivity.

20. The system of claim 19, wherein the means for processing the $T_1$ NMR measurements and the estimate of diffusivity is used to derive formation properties.

21. The system of claim 19, wherein the means for processing the $T_1$ NMR measurements and the estimate of diffusivity is used to derive fluid properties.

22. The system of claim 11, further comprising means for plotting the $T_1$ NMR measurements and an estimate of diffusivity.

\* \* \* \* \*